United States Patent
Santas Gutiérrez et al.

(10) Patent No.: US 11,478,423 B2
(45) Date of Patent: Oct. 25, 2022

(54) SELF-FILM-FORMING COMPOSITION FOR ORAL CARE

(71) Applicant: AB-BIOTICS, S.A., Cerdanyola Del Vallès (ES)

(72) Inventors: Jonatan Santas Gutiérrez, Castelldefels (ES); Elisabet Lázaro Mallén, Barcelona (ES); Jordi Cuné Castellana, Rubí (ES); Javier Mareque Mareque Bueno, Barcelona (ES); Jose Luis Calvo Guirado, Barcelona (ES)

(73) Assignee: AB-BIOTICS, S.A., Cerdanyola del Valles (ES)

(*) Notice: Subject to any disclaimer, the term of this patent is extended or adjusted under 35 U.S.C. 154(b) by 95 days.

(21) Appl. No.: 15/745,264

(22) PCT Filed: Jul. 11, 2016

(86) PCT No.: PCT/EP2016/066456
§ 371 (c)(1),
(2) Date: Jan. 16, 2018

(87) PCT Pub. No.: WO2017/012905
PCT Pub. Date: Jan. 26, 2017

(65) Prior Publication Data
US 2019/0000757 A1    Jan. 3, 2019

(30) Foreign Application Priority Data
Jul. 17, 2015 (EP) .................................... 15177318

(51) Int. Cl.
| | | |
|---|---|---|
| *A61K 9/00* | (2006.01) | |
| *A61K 9/14* | (2006.01) | |
| *A61K 9/19* | (2006.01) | |
| *A61K 35/744* | (2015.01) | |

(52) U.S. Cl.
CPC .......... *A61K 9/0063* (2013.01); *A61K 9/0056* (2013.01); *A61K 9/146* (2013.01); *A61K 9/19* (2013.01); *A61K 35/744* (2013.01)

(58) Field of Classification Search
None
See application file for complete search history.

(56) References Cited

U.S. PATENT DOCUMENTS

2009/0022700 A1 * 1/2009 Cassin .................. A61K 8/731
                                              424/93.42

FOREIGN PATENT DOCUMENTS

| JP | 2010053062 A | * | 3/2010 |
| JP | 2010053062 A | | 3/2010 |
| WO | 2010138522 A2 | | 12/2010 |

OTHER PUBLICATIONS

Toru et al. (JP 2010/053062 A EPO machine translation, published Mar. 11, 2010) (Year: 2010).*
Brachkova et al. "Alginate films containing viable Lactobacillus plantarum: preparation and in vitro evaluation." AAPS PharmSciTech 13.2 (2012): 357-363.
International Search Report in corresponding International Patent Application No. PCT/EP2016/066456, dated Aug. 31, 2016. 4 pages.
International Preliminary Report on Patentability in corresponding International Patent Application No. PCT/EP2016/066456, dated Jan. 23, 2018. 6 pages.

* cited by examiner

*Primary Examiner* — Emily A Cordas
(74) *Attorney, Agent, or Firm* — Leason Ellis LLP

(57) ABSTRACT

A self-film-forming composition in powder form, a reconstituted formula and a kit for oral use are provided, which allow an adequate colonization of the probiotic in the oral cavities together with a sufficient residence time to allow beneficial effects against the pathogens related with oral conditions. Thus, the items provided are useful for the prevention and/or treatment of a condition related to alterations of the oral microbiota, and specifically for peri-implantitis. The self-film-forming composition in powder form comprises at least a gelifier agent and/or at least a bioadhesive agent, and at least one lactic acid bacteria strain.

18 Claims, 6 Drawing Sheets

SELF-FILM-FORMING COMPOSITION FOR ORAL CARE

CROSS-REFERENCE TO RELATED PATENT APPLICATIONS

This application is a U.S. National Phase Application under 35 U.S.C. § 371 of International Patent Application No. PCT/EP2016/066456, filed Jul. 11, 2016, and claims the priority of EP 15177318.1, filed Jul. 17, 2015, all of which are incorporated by reference in their entireties. The International Application was published on Jan. 26, 2017 as International Publication No. WO 2017/012905 A1.

FIELD OF THE INVENTION

The present invention relates to the fields of medicine and microbiology and, particularly, to compositions for use in dental hygiene and therapy. Specifically, the present invention includes compositions for the treatment and/or prevention of peri-implantitis and other oral conditions related with microbial dysbiosis.

BACKGROUND ART

The inflammatory lesions that develop in the tissues surrounding implants are collectively recognized as peri-implant diseases and include two disease entities: mucositis and peri-implantitis. Peri-implantitis and peri-implant mucositis, have similar signs but there is no crestal bone loss in peri-implant mucositis. Mucositis, is defined as a reversible modification of peri-implant soft tissues without bone loss. Peri-implantitis, instead, affects the deep soft tissues and the bone peri-implant, and it has been defined as an inflammatory process that affects the tissues that are close to an osteointegrated implant in such a way to cause a loss of loss of supporting bone, as well as inflammation of the mucosa. The prevalence of peri-implantitis depends on the clinical threshold used to define it, recent results varied between 6.6% and 47% [Albertini, M. et al. 2014].

Peri-implantitis is one of the main causes of implant failure. Plaque accumulation and bacterial unbalance has been proposed as one of the main causes as there is a positive correlation between plaque accumulation and crestal bone loss. Bacteria, stress or a combination of both can stimulate bone loss around an implant in peri-implantitis. Once bone loss increases and a deep pocket is formed, an anaerobic environment that will enhance the predominance of anaerobic bacteria is established. These become then the primary cause of continued bone loss. The microbial composition of biofilms around peri-implantitis has been shown to be different than that present in healthy implants. Overall, the diseased implants present reduced proportion of beneficial bacterial species and increased proportions of putative pathogens compared with healthy implants. Peri-implantitis sites frequently present higher proportions of some recognized periodontal pathogens from the orange complex such as *Fusobacterium nucleatum* or *Prevotella intermedia*. In these sites, other fastidious pathogens from red complex are present including *Porphyromonas gingivalis, Treponema denticola* and *Tannerella forsythia* [Da Silva, E. S. C. et al. 2013]. Albeit being more controversial, it is believed that other mean levels of some periodontal pathogens as *Aggregatibacter actinomycetemcomitans* are commonly associated with peri-implantitis [Persson, G. R. et al. 2013].

Since development of the biofilm on the surface of the dental implants plays an important role in the appearance of peri-implantitis, treatments are mainly based on reducing bacterial colonization on the surface of the implants or mechanically eliminate the bacterial microbiota. Both surgical and nonsurgical techniques have been developed to this effect.

Surgical procedures are based on resection techniques to reduce pocket depth and secure soft tissue morphology and regenerative techniques based on guided bone surgery by using bone placement. In general, these procedures are costly, painful or unpleasant for the patient, thus being restricted as a treatment option when bone loss is advanced or persists despite the initial preventive treatment provided. [Ata-Ali, J. et al. 2011].

Therefore, nonsurgical techniques are preferred as a first-line treatment option. In general terms, these techniques involve the elimination of plaque with chemical plaque control in form of 0.12% chlorhexidine rinses (e.g. 12 hours during 15 days) and/or antibiotics. However, chlorhexidine side effects are well known from time ago. Chlorhexidine may irritate and damage the oral mucosa, causes discolorations and staining of the teeth and other oral surfaces, increases the formation of calculus and alters taste perception. Oral irritation and local allergy-type symptoms have been also reported. Moreover, mucosal side effects have been reported including stomatitis, gingivitis and ulcers. Some of these effects have been ascribed to alterations in the oral microbiota as a result of the antiseptic effect of chlorhexidine [Flötra, L. et al. 1971].

Antibiotic therapy may cause various side effects and drug interaction. For instance, broad-spectrum systemic antibiotics may occasionally develop problems of alterations of commensal microbiota that can lead to antibiotic-associated diseases including *Clostridium difficile*-associated colitis, diarrhea, vaginosis, vaginitis, etc. The use of antibiotic also favors the development of bacterial resistances that may compromise the treatment and may even aggravate further treatments [Slots, J. et al. 1990].

Recent research has turned to probiotics, "live microorganisms which when administered in adequate amounts confer a health benefit on the host". The impact of probiotics on oral health is relatively new with lots of research going on.

An oral probiotic known in the market is *L. reuteri* Prodentis. A recent study indicates that oral treatment with tablets containing the probiotic strain *L. reuteri* induces a significant reduction of pro-inflammatory cytokine response and improvement of clinical parameters in most patients with chronic periodontitis [Szkaradkiewicz, A. K. et al. 2014]. Another study had the aim of evaluating the effects of *L. reuteri*-containing probiotic lozenges as an adjunct to scaling and root planing (SRP) in chronic periodontitis patients. A reduction of *Porphyromonas gingivalis* was observed in the SRP group treated with probiotic but no changes were seen in other studied pathogenic bacteria [Teughels, W. et al. 2013]. However, the effect of *L. reuteri* on the oral microbiota remains questionable since in a parallel study, daily intake of probiotic lozenges containing *L. reuteri* (ATCC55730 and ATCC PTA5289) did not seem to significantly affect plaque accumulation, inflammatory status or microbial composition of the biofilm during experimental gingivitis [Hallstroem, H. et al. 2013].

The recent publication Flichy-Fernandez, A. J. et al. 2015, describes the effect of *L. reuteri* Prodentis probiotic tablets containing the strains *L. reuteri* ATCC PTA5289 and *L. reuteri* DSM 17938, on peri-implant mucositis. Twelve patients with peri-implant mucositis were enrolled in the study and consumed probiotic tablets for 30 days. Patients showed a reduction in gingival index which can be mainly attributed to a reduction of inflammatory cytokines compared to placebo. The document is silent regarding the effect of *L. reuteri* on peri-implantitis. Compared to mucositis, peri-implantitis is characterized by damage in bone structure that is mainly attributed to the effect of pathogenic bacteria. Since the document does not describe the effect of probiotic tablets on peri-implantitis or on related pathogens, it remains questionable whether probiotics may be useful for treating peri-implantitis.

Another example is a recent study describing the effects of orally administered lozenges with *L. rhamnosus* GG and *B. animalis* subsp. *lactis* BB-12 on the amount of plaque, gingival inflammation and the oral microbiota in healthy young adults. The probiotic lozenge decreased both plaque and gingival index, but no probiotic-induced changes were found in the microbial compositions of saliva in either group. The conclusion is that the probiotic lozenge improved the periodontal status in terms of gingival inflammation without affecting the oral microbiota [Toiviainen, A. et al. 2015].

The effect of other probiotics, such as *Lactobacillus brevis* CD2, has been studied in periodontitis but not effect has been demonstrated in peri-implantitis and mucositis [Maekawa, T. et al. 2014]

JP20100053062 discloses oral compositions containing lactic acid bacteria useful for the prevention and/or treatment of oral diseases, including periodontal diseases and caries. Particularly, it is shown that strains of bacteria belonging to *Leuconostoc mesenteroides* species have good coaggregation and adhesion capacity, thus being able to attach to the mucosa and inhibit pathogen biofilm.

Oral compositions can comprise the strains and excipients, binders, lubricants and solubilizing agents formulated according to conventional methods.

A recent review in the field [Yanine, N. et al. 2013] concludes that the effectiveness of probiotics on the prevention and treatment of periodontal diseases is questionable. For the primary outcome, probing pocket depth, there would be no clinical beneficial effect of probiotics. For secondary outcomes, probiotics have shown small benefits on plaque index and gingival inflammation. In summary, it has been seen in the prior art that probiotics may contribute in the improvement of inflammation in periodontal and gingival processes, but it remains questionable whether probiotics can have an effect in the dysbiosis present in such processes which is the main cause of bone loss in peri-implantitis.

A further problem associated with the efficacy of the current therapies, is that the techniques and methods used for oral delivery of probiotics, including incorporation in foods, tablets, chewing gums, gels or toothpastes, have important limitations. These include negative effects on the stability of the probiotic and a reduction of their capacity to elicit beneficial effect due to their short residence time in the oral cavity. This is a challenge when probiotics have to be delivered in inaccessible cavities of the mouth, such as sites around the dental implants, which may compromise their antagonistic activity against oral pathogens to prevent or treat peri-implantitis.

Moreover, the areas of the implant that are contiguous to the bone have often a raw surface to assist implant adhesion and osteointegration, and can remain contaminated also after an antimicrobial treatment has been made, with subsequent further bone loss and formation of a peri-implant pocket. Efforts to manage pathogenic colonization of these areas have been met with limited success. Dental hygiene has been proven ineffective since these areas are inaccessible and smaller than most brush and other devices. Systemic prophylactics have limited effects since bacteria tend to rapidly aggregate into protected clusters, increasing the chance of generating antibiotic-resistant bacteria.

A delivery system capable of delivering probiotic bacteria in specific desired sites of the oral cavity is required for the efficient modulation of the oral microbiota. A delivery system should allow a slow release of viable and metabolically active probiotic bacteria to the oral cavity, an adequate colonization of the probiotic in the desired sites together with a sufficient residence time to allow beneficial effects.

SUMMARY OF THE INVENTION

One problem to be solved by the present invention may be seen as related to the provision of a delivery system capable of delivering probiotic bacteria in specific desired sites of the oral cavity, required for the efficient modulation of the oral microbiota involved in pathological conditions at such sites.

The solution is based on the provision of a composition in powder form, a reconstituted formula and a kit for oral use, which allow an adequate colonization of the probiotic in the desired sites together with a sufficient residence time to provide beneficial effects against the pathogens related with oral conditions.

Accordingly, a first aspect of the invention relates to a self-film-forming composition in powder form, self-film-forming under agitation in the presence of a liquid medium, the composition comprising: (i) at least one gelifier agent in powder form, (ii) at least one bioadhesive agent in powder form, and (iii) at least one lactic acid bacteria strain in powder form, wherein (i), (ii) and (iii) are in a single or in separate containers, and wherein the self-film-forming composition is administered topically.

Thus, the invention provides a self-film-forming composition in powder form, wherein the self-film is formed under agitation in the presence of a liquid medium.

The term "film-forming" means that is capable of forming a film upon application to a solid surface; i.e. that leaves a pliable, cohesive, and continuous covering over a surface. The term "self-film-forming" means that no other component or condition further to the indicated ones is needed to form a film. "Under agitation" is widely understood in this description, including manual agitation or by means of an electric mixer; with continuous or discontinuous agitation, and during a suitable period of time that preferably is comprised between 5 seconds to 60 minutes, more preferably from 10 seconds to 30 minutes or from 30 seconds to 10 minutes.

The film is formed over a surface either by increasing the viscosity of the composition with a gelifier agent and by increasing the adhesiveness of the composition with a bioadhesive agent. The term "gelifier agent" relates herein to a substance that increases the viscosity of a liquid, forming a gel. They are able to dissolve in the liquid phase as a colloid mixture that forms a weakly cohesive internal structure. It can also be referred in the art as thickener, stabilizer, or emulsifier. The term "bioadhesive agent" refers to naturally-occurring polymers that act as adhesives, i.e. that, applied to the surfaces of materials, bind them together and resist separation. Preferred gelifier and bioadhesive agents are discussed further in detail below.

Without being limited to theory, it is believed that the solution herein proposed enables on one hand the delivery of the lactic acid bacteria (preferably with probiotic properties) in inaccessible cavities of the mouth, such as the cavities surrounding the dental implants and the gaps and the raw surface of the implant itself, which are usually contaminated with pathogenic bacteria. As a second advantageous point, the solution hereby proposed allows an adequate colonization of the probiotic in the desired sites together with a sufficient residence time to allow beneficial effects against the pathogens related with oral conditions. More particularly, the gelifier and bioadhesive agents included in the composition, enable and enhance the growth of the lactic acid bacteria at the desired sites, thus forming a beneficial biofilm that seal the problematic cavities (i.e. forms a physical barrier against further pathogen contamination). Remarkably, the prebiotic effect of the gelifier agent and the bioadhesive agent is negligible in the case of the pathogenic bacteria, which is of interest for avoiding the undesirable growth of pathogens. Thus, while the development of the beneficial probiotic biofilm is enhanced, the development of the pathogenic biofilm is reduced. Therefore, the formation of the probiotic biofilm together with the antagonistic activity of the lactic acid bacteria against oral pathogens stops the vicious circle derived from the action of the pathogenic bacteria, i.e. the bone loss in the peri-implant area.

Second and third aspects of the invention relate to a process for preparing a reconstituted formula comprising mixing under agitation a self-film-forming composition in powder form of the first aspect with a liquid medium, and the reconstituted formula obtained thereof.

A fourth aspect of the invention relates to a kit for oral use, comprising: (1) the self-film-forming composition in powder form of the first aspect, or the reconstituted formula of the third aspect; and (2) means to apply to the buccal cavity the self-film-forming composition in powder form or the reconstituted formula.

A fifth aspect of the invention relates to a self-film-forming composition in powder form, or the reconstituted formula, for use as a medicament.

A sixth aspect of the invention relates to the self-film-forming composition in powder form of the first aspect, or the reconstituted formula of the third aspect, for use in the prevention and/or treatment of a condition selected from the group consisting of: peri-implantitis, mucositis, periodontitis, gum disease, caries, oral candidiasis, cold sores and blisters.

A seventh aspect relates to the non-medicament use of the self-film-forming composition in powder form or the reconstituted formula, for oral care.

An eighth aspect of the invention relates to an isolated strain belonging to genus *Pediococcus* for use in the prevention and/or treatment of a condition selected from the group consisting of peri-implantitis and mucositis.

A ninth aspect of the invention relates to an isolated strain belonging to genus *Pediococcus* deposited in the Spanish Type Culture Collection selected from the group consisting of: strain deposited under accession number CECT 8903, strain CECT 8904, strain CECT 8905, strain CECT 8906.

A tenth aspect of the invention relates to a self-film-forming composition in powder form, self-film-forming under agitation in the presence of a liquid medium, the composition comprising: (i) at least one agent in powder form selected from the group consisting of a gelifier agent and a bioadhesive agent, and (ii) at least one *Pediococcus* strain in powder form, wherein (i) and (ii) are in a single or in separate containers.

Eleventh and twelfth aspects of the invention relate to a process for preparing a reconstituted formula comprising mixing under agitation a self-film-forming composition in powder form of the tenth aspect with a liquid medium, and the reconstituted formula obtained thereof.

A thirteenth aspect of the invention relates to a kit for oral use, comprising: (1) the self-film-forming composition in powder form of the tenth aspect, or the reconstituted formula of the twelfth aspect; and (2) means to apply to the buccal cavity the self-film-forming composition in powder form or the reconstituted formula.

A fourteenth aspect of the invention relates to the self-film-forming composition in powder form of the tenth aspect, or the reconstituted formula of the twelfth aspect, for use in the prevention and/or treatment of a condition selected from the group consisting of: peri-implantitis, mucositis, periodontitis, gum disease, caries, oral candidiasis, cold sores and blisters.

The detailed description and examples shown below are presented for the purposes of providing those skilled in the art with a sufficiently clear and complete explanation of this invention, but should not be considered limitations on the essential aspects contemplated therein, as presented in earlier sections of this description.

DETAILED DESCRIPTION OF THE INVENTION

The invention provides self-film-forming compositions in powder form comprising lactic acid bacteria and process for their preparation comprising mixing with a liquid medium.

In one aspect, the self-film-forming composition comprises at least one gelifier agent, at least one bioadhesive agent and at least one lactic acid bacteria strain. In another aspect, the self-film-forming composition comprises at least one gelifier or at least one bioadhesive agent, and at least one *Pediococcus* strain.

Self-Film-Forming Composition in Powder Form

The lactic acid bacteria included in the self-film-forming composition in powder form of the invention can be in form of viable or non-viable cells. The general use of strains is in the form of viable cells. However, it can also be extended to non-viable cells such as killed cultures or cell lysates (obtained by e.g. exposure to altered pH, sonication, radiation, temperature, pressure, or among other means of killing or lysing bacteria) or compositions containing beneficial factors previously produced by any of the strains (e.g. bacteriocins and anti-inflammatory substances).

In a particular embodiment, the at least one lactic acid bacteria strain included in the powder composition is in a form that comprises viable cells. This means that the composition is substantially composed of viable cells or partially composed by viable cells.

In a particular embodiment, the at least one agent in powder form selected from the group consisting of a gelifier agent and a bioadhesive agent have no bactericidal effect against the at least lactic acid bacteria. The term "bactericidal", also known as "bacteriocidal", means that kills bacteria, i.e. reduces the number of viable cells in the composition. Thus, the agents included in the composition are those that do not kill the lactic acid bacteria. It is known by the skilled in the art that the number of viable cells in a product containing bacteria decreases naturally over time depending on the storage conditions including temperature, atmosphere, and use of protective agents such as cryoprotectants or other carriers. In this description, the expression "have no bactericidal effect" means that the concentration of viable cells in the presence of the gelifier and/or the bioadhesive agent is not reduced compared to the concentration of viable cells in the absence of these agents when stored or incubated under the same conditions.

Preferably, the concentration of viable cells in the powder composition in the presence of the gelifier and/or the bioadhesive agent compared to the same composition without these agents, is reduced no more than 10000 times (i.e. 4 logarithms). This means that if, for example, the concentration of viable cells in the powder not containing the gelifier and bioadhesive agents is 1E+09 cfus/g, the concentration of viable cells in the presence of the agents is not lower than 1E+05 cfus/g.

More preferably, the concentration of viable cells in the powder composition in the presence of these agents is reduced no more than 1000 times (3 logs), 100 times (2 logs) or 10 times (1 log) compared to the same composition without these agents.

In a particular embodiment, besides having no bactericidal effect, the gelifier and bioadhesive agents have no bacteriostatic effect against the lactic acid bacteria. This means that the agents do not kill the bacteria, nor inhibit the growth of the bacteria (they do not stop bacteria from growing and dividing). Thus, the agents included in the composition are those that do not prevent bacteria from growing normally.

In a more particular embodiment, the agents are those that have a prebiotic effect. This means that they improve or enhance the growth of the bacteria. This feature is shown in EXAMPLES 5-7 below.

In an even more particular embodiment the prebiotic effect of the agent of interest is studied by incubating the lactic acid bacteria of interest in the presence of the agent. Artificial saliva containing 1 g/L 'Lab-lemco' powder (Oxoid, Basingstoke, UK), 2 g/L yeast extract (Oxoid), 5 g/L proteose peptone (Oxoid), 2.5 g/L hog gastric mucin (Sigma Chemical Co., Poole, UK), 35 g/L sodium chloride (BDH Chemicals Ltd, Poole, UK), 0.2 g/L calcium chloride (BDH), 0.2 g/L potassium chloride (BDH) in distilled water is supplemented with the agent of interest to a final concentration of 0.5% (w/v). Artificial saliva without gel ingredient is also prepared to compare the effect of the agent of interest in bacterial growth with a non-supplemented medium. After autoclaving, 1.25 mL of 40% urea in water (w/v) per liter of artificial salivary medium is added. Two hundred microliters of the different media prepared are pipetted in 96-well plates. Immediately after 20 microliters of a suspension of lactic acid bacteria of interest standardized to 1E+07 CFU/mL in PBS is added. The same amount of PBS without bacterial inoculum is used as a negative control. Plates are incubated for 24 h at 37° C. in anaerobiosis and bacterial growth monitored by determining the optical density at 625 nm. The capacity of probiotic candidates to use the agent of interest for growing is calculated according to the following formula:

$$\Delta\text{Growth}=(\Delta DO_{gp}-\Delta DO_{g0})-(\Delta DO_{sp}-\Delta DO_{s0})$$

wherein $\Delta DO_{gp}$ is the difference between the optical density at 625 nm after 24 h compared with 0 h in the wells supplemented with the agent of interest and inoculated with lactic acid bacteria (LAB) candidates of interest;

$\Delta DO_{g0}$ is the difference between the optical density at 625 nm at 24 h compared with 0 h in the wells supplemented with the agent of interest but containing PBS instead of LAB;

$\Delta DO_{sp}$ is the difference between the optical density at 625 nm at 24 h compared with 0 h in the wells not supplemented with the agent of interest and inoculated with LAB; and $\Delta DO_{s0}$ is the difference between the optical density at 625 nm at 24 h compared with 0 h in the wells not supplemented with the agent of interest and containing PBS instead of LAB.

Based on the detailed assays described in EXAMPLES 5-7 the skilled person is routinely able to repeat the assay to objectively determine whether a particular agent of interest has a prebiotic effect. It is relevant to note that the description and conditions of assays disclosed in EXAMPLES 5-7 are not limiting the scope of the invention. The assays are ones suitable to test the ability of the agents of interest to test their prebiotic effect.

In a particular embodiment, the agent is considered to have a prebiotic effect when the Δ Growth determined as described above is higher than 0.005. In a more particular embodiment the Δ Growth is higher than 0.01. In an even more particular embodiment the Δ Growth is higher than 0.02.

As discussed above, the composition in powder form comprises at least one agent that can be a gelifier agent. In a particular embodiment the at least gelifier agent is in an amount to provide viscosity to the composition, and is selected from the group consisting of:

(a) a starch, preferably rice, corn, potato starch or sodium starch glycolate;

(b) a gum, preferably tragacanth gum, acacia gum, xanthan gum, ghatti gum, gellan gum, karaya gum, konjac gum, or galactomannan gum (particularly guar gum, locust beam gum, and tara gum);

(c) an algal polysaccharide, preferably alginic acid, sodium alginate, agar, dextran or carrageenan;

(d) a polysaccharide selected from the group consisting of pectin and maltodextrin;

(e) a cellulose derivative, preferably methylcellulose, carboxymethylcellulose, sodium or calcium carboxymethylcellulose, hydroxyethylmethylcellulose, hydroxypropylmethylcellulose, ethylhydroxyethylcellulose, ethylmethylcellulose, hydroxyethylcellulose, cellulose acetate phthalate or microcrystalline cellulose;

(f) a polypeptide selected from the group consisting of gelatin, collagen, and casein; and (g) a polymer selected from the group consisting of an acrylate-base polymer, a vinyl-based polymer (preferably polyvinylpyrrolidone, also known as polyvidone or povidone), a cationic polysaccharide (e.g. cationic acetyl-glucosamine, preferably chitosan, cationic cyclodextrin and cationic dextran), and a polyalkylene glycol (preferably polyethyleneglycol).

The at least one agent can also be a bioadhesive agent. Particularly, the bioadhesive agent is in an amount to provide adhesiveness to the composition, and is selected from the group consisting of:

(a) a gum, preferably hakea gum, xanthan gum, acacia gum, konjac gum, gellan gum, or galactomannan gum (particularly guar gum);

(b) an algal polysaccharide, preferably alginic acid, sodium alginate, agar, dextran or carageenan;

(c) a cellulose derivative, preferably, methylcellulose, carboxymethylcellulose, hydroxymethylcellulose, hydroxypropylcellulose, hydroxypropylmethylcellulose, methylhydroxyethylcellulose, hydroxyethylcellulose;

(d) a polysaccharide selected from the group consisting of pectin and maltodextrin; and (e) a polymer selected from the group consisting of an acrylate-base polymer, a vinyl-based polymer (preferably polyvinylpyrrolidone or povidone), a cationic polysaccharide (preferably chitosan), and a polyalkylene glycol (preferably polyethyleneglycol).

As mentioned before, the gelifier agent is in an amount to provide viscosity to the composition and the bioadhesive agent is in an amount to provide adhesiveness to the composition. The compounds used as gelifier and bioadhesive agents are well known in the art, so the amounts of agents will be determined by the skilled in the art. In a particular embodiment, the gelifier agent is a gum. The gum may be, for example, xanthan gum, Arabic gum, guar gum, tragacanth gum, gum karaya, locust bean gum, carob bean gum, acacia gum, ghatti gum, gellan gum, karaya gum, konjac gum, hakea gum and tara gum. Such gums may be generally classified as carbohydrate gums that have an overall negative charge. More preferably, the gelifier agent is guar gum, also known in the field as gum cyamopsis, guar flour, and guaran. Guar gums are extracted from the endosperm of seeds of certain plants of the family of legumes. They are galactomannans resulting from the linear chain formation of D-mannose units bonded at (1-4), with branches formed by a single D-galactose bonded at (1-6). Guar gum can be modified or derivatized. Examples of guar gum derivatives are hydroxypropylated or carboxyhydroxypropylated derivatives, cationic derivatives (Ecopol) and the products resulting from the depolymerization of guar gums.

In a particular embodiment, the bioadhesive agent is a cellulose derivative. The main derivatives are cellulose ethers, i.e. alkyl modifications of cellulose, resulting from substituting part of the hydrogen atoms of the hydroxyl groups of the anhydrous glucose units with alkyl groups. Non limiting examples of cellulose ethers are: methylcellulose (MC), hydroxyethylmethylcellulose (HEMC), hydroxypropylcellulose (HPC), hydroxypropylmethylcellulose (HPMC), hydroxyethylcellulose (HEC), ethylhydroxyethylcellulose (EHEC), ethylcellulose, sodium carboxymethylcellulose (CMCNa), quaternary ammonium salts of hydroxyethylcellulose with a trimethylammonium substituent (Polyquaternium 10), and dimethyldiallylammonium chloride copolymers (Polyquaternium A). In a more preferred embodiment, the bioadhesive agent is hydroxyethylcellulose (HEC).

Non limiting examples of starches include pregelatinized starch (corn, wheat, tapioca), pregelatinized high amylose content starch, pregelatinized hydrolyzed starches (maltodextrins, corn syrup solids), or chemically modified starches such as pregelatinized substituted starches (e.g. octenyl succinate modified starches).

In a particular embodiment, the self-film-forming composition in powder form comprises at least one gelifier agent and at least one bioadhesive agent. In a more particular embodiment, the gelifier agent is a compound different from the bioadhesive agent.

In a particular embodiment, the gelifier agent is selected from the group consisting of a gum and an algal polysaccharide and the bioadhesive agent is selected from the group consisting of a cellulose derivative and a vinyl-based polymer.

More particularly, the gelifier agent is guar gum or alginate and the bioadhesive agent is hydroxyethylcellulose (HEC) or polyvinylpyrrolidone.

Thus, in a particular embodiment, the gelifier agent is selected from the group consisting of guar gum and sodium alginate, and the bioadhesive agent is HEC.

The self-film-forming compositions according to the invention are in powder form. Particularly, that means that the composition has a water content less than 10%, more preferably less than 5%.

The skilled person will routinely select the amounts of gelifier and bioadhesive agents in powder form to obtain a reconstituted formula providing an appropriate viscosity and adhesiveness degree depending on the volume of the reconstituted formula.

In a particular embodiment, the amounts of gelifier agent and bioadhesive agent in the self-film-forming composition are the amounts necessary to obtain concentrations of each agent from 0.05 to 20% (w/v) in the final reconstituted formula. More particularly, the gelifier agent in powder form is in an amount to obtain a concentration from 1 to 5% (w/v), more particularly a 2%, 3% or 4% (w/v) in the final reconstituted formula and the bioadhesive agent in powder form is in an amount to obtain a concentration from 4 to 10% (w/v), more particularly a 6% (w/v) in the final reconstituted formula.

In a particular embodiment for peri-implantitis application, the self-forming-composition comprises the necessary amount of guar gum and HEC to obtain a final reconstituted formula comprising a 4% (w/v) of guar gum and 6% (w/v) of HEC. In a particular embodiment for dental application, the self-forming-composition comprises the necessary amount of guar gum and HEC to obtain a final reconstituted formula comprising a 2% (w/v) of guar gum and 6% (w/v) of HEC.

In a particular embodiment, the composition in powder form comprises between 0.05 and 90% of gelifier agent (w/w), more particularly from 1% to 60% (w/w). In more particular embodiments the amount of gelifier agent is 50%, 20%, 15% and 10% (w/w). In another particular embodiment, the amount of bioadhesive in the composition in powder form is comprised between 0.05 and 90% (w/w), and particularly between 30 and 85% (w/w). In more particular embodiments the amount of bioadhesive is 68%, 50% and 40% (w/w).

The skilled person will select the appropriate volumes of liquid medium according to the surface and condition to be treated. In a particular embodiment, the volume used to reconstitute the formula is no higher than 500 mL. In a particular embodiment the volume used is no higher than 200 mL, 150 mL, 100 mL, 50 mL or 20 mL. In a more particular embodiment the volume used to reconstitute the formula is 6 mL. In a more particular embodiment the volume used to reconstitute the formula is in the range from 2 to 3 mL.

The skilled in the art will find below (section Reconstituted formula and process to obtain it) non-limiting examples of appropriate amounts of gelifier and bioadhesive agents in powder form, final reconstituted formula and volumes of liquid medium.

Gelifier and bioadhesive agents and the amounts used in the present invention are not used as mere carriers, excipients, binders, lubricants, surfactants or solubilizing, wetting agents, but selected to confer appropriate viscosity and adhesiveness properties to the final reconstituted compositions to improve the administration of lactic acid bacteria. Appropriate combinations allow to administer the lactic acid bacteria without decreasing their efficacy and stability, or even increasing it, in a period of time convenient for clinical practice.

As discussed above, the self-film-forming composition in powder form of the invention also comprises at least one lactic acid bacteria strain. In a particular embodiment, the lactic acid bacteria strain is able to antagonize at least one oral pathogen selected from the group consisting of bacteria of the genus: *Porphyromonas, Fusobacterium, Prevotella,* and *Aggregatibacter*. More particularly, it is able to antagonize at least one oral pathogen selected from the group consisting of: *Porphyromonas gingivalis, Fusobacterium nucleatum, Prevotella intermedia,* and *Aggregatibacter actinomycetemcomitants*. The ability of the lactic acid bacteria strain to antagonize oral pathogens is tested for example with the assay of EXAMPLES 8-9.

In a particular embodiment, the lactic acid bacteria strain is selected from the group consisting of bacteria of the genus: *Pediococcus, Lactobacillus, Bifidobacterium, Streptococcus, Lactococcus, Enterococcus, Bacillus, Bacteroides, Propionibacterium,* and *Leuconostoc*. Particularly, the lactic acid bacteria is a *Lactobacillus* (e.g. *Lactobacillus reuteri, Lactobacillus brevis, Lactobacillus rhamnosus,* or *Lactobacillus plantarum*), a *Bifidobacterium,* or a *Streptococcus*. More particularly, the lactic acid bacteria strain belongs to genus *Pediococcus*. More particularly, the strain is a *Pediococcus acidilactici* or a *Pediococcus pentosaceus*. More particularly, the lactic acid bacteria strain is selected from the group consisting of: strain CECT 8903, strain CECT 8904, strain CECT 8905, and strain CECT 8906.

As indicated above, the at least gelifier agent, the at least bioadhesive agent and the at least lactic acid bacteria strain forming the composition in powder form are in a single or in separate containers. The method to obtain the compositions of previous aspects comprises: obtaining the lactic acid bacteria strain by culturing it in a suitable medium and processing it into powder form (for instance freeze-drying it), and mixing the lactic acid bacteria strain with the gelifier agent and the bioadhesive agent, both in powder form, if the composition is presented in a single container. Methods to culture and post-treat the lactic acid bacteria are described below. The composition can be also presented in three or two different containers comprising the elements of the composition, and they can be mixed by the user before application.

The self-forming composition is especially suitable for topical administration. The term "topical" as used herein means application to body surfaces such as the skin or mucous membranes, either being external or internal. Not limiting examples of topical routes of administration are epicutaneous administrations (applied directly to the skin), application to eye conjunctiva or application to the ear, administration to oral surfaces (e.g. teeth and gum) or vaginal administrations.

Reconstituted Formula and Process to Obtain it

As discussed above, an aspect of the invention relates to a process for preparing a reconstituted formula comprising mixing under agitation the self-film-forming composition in powder form of previous aspects with a liquid medium. A reconstituted formula is obtained. The agitation can be performed by manual agitation or by means of an electric mixer; with continuous or discontinuous agitation, and during a suitable period of time. The mixing period preferably is comprised between 5 seconds to 60 minutes, more preferably from 10 seconds to 30 minutes or from 30 seconds to 10 minutes. In a more preferred embodiment, agitation is performed for 1, 2, 3, 4 or 5 minutes. The formula is reconstituted preferably just before use and allowed to stand for gelifying previous to its administration. In a particular embodiment, after mixing, the composition is allowed to stand from at least 10 seconds. More particularly, the reconstituted formula is allowed to stand for at least 30 seconds, more particularly at least 1 minute before application. It can also be convenient to avoid long periods of time in order to avoid that the gel becomes too dense previous to its application, which may difficult its distribution on the surface to be treated. Therefore, in a particular embodiment the formula, once reconstituted is applied on the surface to be treated in a period of time not longer than 120 minutes. More particularly, the reconstituted formula is applied in a period of time no longer than 60 minutes, more particularly no longer than 30 minutes, more particularly no longer than 10 minutes.

The liquid medium is preferably water acceptable for human or animal consumption. However, the liquid medium is also e.g. any suspension in water, an oil, glycerol, or a vaseline.

The reconstituted formula can preferably adopt the form of a gel with suitable viscosity and/or adhesiveness to be applicable to the desired oral cavity, the form of a varnish if for example the formula is to be applied on the dental surface, or the form of a spray.

The amounts of gelifier agent and bioadhesive agent in the final reconstituted formula are from 0.05 to 20% (w/v) for each agent. Preferably, the reconstituted formula comprises 1-5% (w/v) of gelifier, more preferably a 2%, 3% or 4% (w/v of the total reconstituted formula) and 1-10% (w/v) of bioadhesive, more preferably a 4-10% (w/v), more preferably a 6% (w/v of the total reconstituted formula).

In a particular embodiment for peri-implantitis application, the reconstituted formula particularly comprises 4% w/v guar gum and 6% of HEC. In a particular embodiment for dental application, the reconstituted formula comprises 2% w/v of gum guar and 6% of HEC.

A preferred composition in powder form comprises 20% (w/w) of guar gum and 30% of HEC, and the lactic acid bacteria is in an amount of 50%. If 0.5 g of the powder blend is reconstituted with 2.5 ml of water, the final concentrations in the gel are 4% (w/v) of guar gum and 6% of HEC.

A preferred composition in powder form comprises 10% (w/w) of guar gum and 30% of HEC, and the lactic acid bacteria is in an amount of 60% (w/w). If 0.5 g of the powder blend is reconstituted with 2.5 ml of water, the final concentrations in the gel are 2% of guar gum (w/v) and 6% of HEC.

In another embodiment, the composition in powder form comprises 15% (w/w) of sodium alginate, 30% of HEC and 1.5% of calcium acetate, and the lactic acid bacteria is in an amount of 53.5% (w/w). If 0.5 g of the powder blend is reconstituted with 2.5 ml of water, the final concentrations in the gel are 3% (w/v) of alginate and 6% of HEC.

In another embodiment, the composition in powder form comprises 10% (w/w) of sodium alginate, 30% of HEC and 1% of calcium acetate, and the lactic acid bacteria is in an amount of 59% (w/w). If 0.5 g of the powder blend is reconstituted with 2.5 ml of water, the final concentrations in the gel are 2% of alginate and 6% of HEC.

In another embodiment, the composition in powder form comprises 20% (w/w) of guar gum and 10% of polyvinylpyrrolidone, and the lactic acid bacteria is in an amount of 70% (w/w). If 0.5 g of the powder blend is reconstituted with 2.5 ml of water, the final concentrations in the gel are 4% of guar gum (w/v) and 2% of polyvinylpyrrolidone.

In another embodiment, the composition in powder form comprises 50% (w/w) of guar gum and the lactic acid bacteria is in an amount of 50% (w/w). If 0.5 g of the powder blend is reconstituted with 6 ml of water, the final concentration of guar gum in the gel is 4% (w/v).

In another embodiment, the composition in powder form comprises 72% (w/w) of HEC and the lactic acid bacteria is in an amount of 28% (w/w). If 0.5 g of the powder blend is reconstituted with 6 ml of water, the final concentration of HEC in the gel is 6%.

Kit for Oral Use

A particular embodiment of the invention is an article of manufacture comprising a sealed container having enclosed the powder composition as herein provided, preferably in a unit dosage amount and in a sterile condition. The container preferably has a capacity sufficient to enable reconstitution of the composition in situ. Generally, a capacity of about 1 ml to about 20 ml, preferably about 5 ml to about 10 ml, will be found convenient.

Thus, in some cases, the article of manufacture is only the container with the self-film-forming composition in powder form, because the professional has at his disposal the other elements to use and apply the self-film-forming composition to the patient (e.g. liquid medium, syringe and needle, and means for application).

Another article of manufacturer is the reconstituted formula which can be stored refrigerated for a short period of time until use.

However, in some cases, the article of manufacture is a kit comprising other elements to facilitate the use and the application. Accordingly, another aspect of the invention relates to a kit for oral use, comprising: (1) the self-film-forming composition in powder form as defined above; or the reconstituted formula; and (2) means to apply to the buccal cavity the self-film-forming composition in powder form, or the reconstituted formula.

The self-film-forming composition in powder form could be applied directly to the oral cavity and reconstituted in situ with the saliva for example. Nevertheless, a preferred embodiment is to reconstitute the composition just before use.

In a particular embodiment, the means for application to the buccal cavity are selected from the group consisting of: a brush, a syringe with an injection needle, a syringe with a blunt tip needle, and a mouth guard.

In a more particular embodiment, the means for application is a syringe and a needle that has a blunt tip similar to a periodontal probe. By means of the syringe and the blunt tip needle, the reconstituted solution is applied into the affected region, i.e. into a peri-implant pocket.

The means for application is a mouthguard, also known as occlusal splints, mouthprotector, mouth piece, gumshield, gumguard, nightguard, bite or mouth splint, or bite plane. This is a removable dental appliance to fit the upper or lower arches of teeth. The mouthguard or mouth splint is filled with the composition in powder form or the reconstituted formula and is fitted to the teeth.

In another embodiment, in order to facilitate the use, the kit further comprises a container with a liquid medium to reconstitute the self-film-forming composition in powder form.

In another embodiment, also in order to facilitate the use, the kit further comprises means for putting the liquid into the container with the self-film-forming composition in powder form. The means are preferably a syringe equipped with a disposable perforating needle that is used for drawing the liquid from its container and putting into the container with the self-film-forming composition in powder form.

The term "container" herein is used to denote any small recipient, having a closure that is suitable for packaging a unit dosage amount of a reconstitutable powder, preferably in a sterile condition. It will be understood that equivalent forms of packaging, such as a vial, an ampoule, a disposable syringe, a syringe cartridge or a pre-filled syringe, are encompassed by this embodiment of the invention. Optionally the vial can be a multicompartment vial comprising e.g. two compartments, one to contain the reconstitutable powder and one to contain a liquid in an amount sufficient to dissolve the powder. In such a vial the two compartments are interconnected by an aperture wherein a stopper can be engaged to prevent contact of the powder and the solvent liquid until the vial is ready for use. In use, the liquid is brought into contact with the powder by disengagement or puncture of the stopper by any suitable means, for example a device such as a plunger that exerts pressure or drives a needle through the stopper. Examples of such multi-compartment vials include a dual-chamber cartridge for a syringe and a dual-chamber vial, or a delivery cap and a vial closed with this cap.

A particular implementation of the invention consists of the following steps: an amount of the self-film-forming composition of the invention in powder form is introduced into a glass vial provided with a septum and aluminum capsule. Upon the addition of water with a syringe, preferably deionized or distilled water, and manual shaking, the reconstituted gel is formed in very short time. This gel does not have a very high viscosity for being applied by means of a syringe and has suitable adhesiveness for dental implant applications. The reconstituted formula is then administered e.g. with a syringe and needle, brush, or pressure applicator to a periodontal pocket or surgical site. The dental professional is able to manipulate the system to gain optimum conformity to the treatment site and overcome placement difficulties inherent in other systems. When administered the slightly film system remains in the desired site, thus being possible to seal the desired implant interior spaces with the formula of the invention.

Medical Applications

As discussed above, another aspect of the invention relates to the self-film-forming composition in powder form, or the reconstituted formula, for use as a medicament. Particularly, the invention provides the self-film-forming composition in powder form or the reconstituted formula, for use in the prevention and/or treatment of a condition related to alterations of the oral microbiota. More particularly, this condition is selected from the group consisting of: peri-implantitis, mucositis, periodontitis, gum disease, caries, oral candidiasis, cold sores and blisters. In a particular embodiment, the condition is peri-implantitis.

These aspects can be alternatively formulated as the use of any of the compositions of the invention for the manufacture of a pharmaceutical product, a veterinary product, a medicament, a food product, a food supplement, a medical food, or an oral care product for the prevention and/or treatment of a condition related to alterations of the oral microbiota, preferably peri-implantitis, mucositis, periodontitis, gum disease, caries oral candidiasis, cold sores and blisters. This may be also alternatively formulated as a method for the prevention and/or treatment of a condition related to alterations of the oral microbiota, comprising administering to the subject in need thereof an effective amount of any of the compositions of the invention.

Application in the Treatment and Prevention of Peri-Implantitis

Dental prosthesis generally include two components: The implant component (also known as an endosseous implant or fixture) is a screw embedded into the osteotomy. It is the portion that lies below the gum line and can be considered an artificial tooth root. The other component is the crown, bridge, or denture, which is fixed to the implant component and in the case of the crown substitutes the visual part of the tooth. A third component can be included, an abutment, which is a ceramic or titanium component that ensures a secure fit between the dental implant and the crown. The abutment portion is that part that lies at and above the gum line. Between these structures are gaps and cavities into which bacteria can penetrate from the oral cavity. Later these bacteria can return into the adjacent tissue and can cause peri-implantitis.

As specific implementation of the invention in the prevention and treatment of peri-implantitis, upon the addition of water with a syringe to the container with the self-film-forming composition in powder form, and manual shaking, the reconstituted gel is formed in very short time. The reconstituted gel is administered for example, with a syringe and needle with blunt tip to the gaps, microgaps and cavities of the implant. In particular, since the dental implant comprises a raw surface that is exposed to oral fluids, because a vertical bone loss has occurred and due to the local inflammatory process a peri-implant pocket has been created, the above described composition is applied in such pocket, in such a way that it adheres to the raw surface of the implant and to the mucous surface of the pocket same. Therefore, the solution can be advantageously applied into a peri-implant pocket by bending the blunt tip needle, mimicking a periodontal probe, positioning the tip of the blunt needle close to the base of the pocket and injecting the product until the solution reaches the upper edge of the gum.

Advantageously, the above-described self-film-forming composition is associated with means for administering it to the peri-implant region close to a dental implant that is affected by the inflammatory process, in particular, the composition is associated with a dental kit which comprises a flexible blunt needle.

Particularly, a specific implementation of the invention in the treatment of peri-implantitis consists of: removing the crown; administering local anesthesia to the patient; cleaning the zone to be treated; removing mechanically the subgingival plaque by scraping; applying an antibiotic such as chlorhexidine; applying saline solution; and applying the reconstituted formula of the invention in the surroundings and cavities of the implant and also inside the implant. After drawing the needle out of the pocket, saline solution washings and an air jet (during ca. 10 sec.) are applied on the treated zone. Immediately after, the crown is put in place. The patient is instructed not to brush the teeth within 6 hours post-treatment.

In case of a preventive treatment, it particularly consists of: removing the crown; optionally cleaning the zone to be treated and removing mechanically the subgingival plaque by scraping; and applying the reconstituted formula of the invention.

Other Oral Applications: Gingivitis and Dental Caries

The invention can also be used in the dental hygiene of healthy subjects to prevent potential diseases, and in the treatment or prevention of oral conditions related with oral dysbiosis, besides peri-implantitis.

In a particular embodiment, the solutions of the invention are used in the prevention and treatment of periodontitis and gingivitis. The onset of gingivitis and inflammation of the periodontium and periodontal disease is usually associated with a shift of the microbial balance in the sulcus, i.e. around the tooth cavity between the tooth surface and gums. It results in the formation of bacterial plaques (biofilms), and an increased presence of Gram-negative pathogenic species within these deposits. The exotoxins and metabolites produced by these bacteria accumulate and cause inflammation of the surrounding gum tissue, which in turn leads to swelling and bleeding. In the course of inflammation, the liability of the junctional epithelium is weakened to the tooth so that bacteria can penetrate the subgingival area. Periodontal disease also occurs to most mammals, especially in horses, cats, rodents, livestock and dogs. For example, 80% of all dogs over the age of 3 years have periodontal disease.

Periodontal therapy is typically first removing mechanically the subgingival plaque by scraping or by ultrasound; by this mechanical removal, the bacteria in the biofilm are released and flushed out. In the course of this treatment, antibiotics and other bactericidal compositions are used today, which are designed to prevent the re-colonization by gram-negative bacteria. The disadvantage of a regular and extensive use of compositions containing antibiotics, however, is the risk of developing antibiotic resistance and the often triggered side effects of these products. As in the case of peri-implantitis, the reconstituted formulas of the invention can be e.g. applied by means of a syringe, particularly with a blunt tip needle.

In another particular embodiment, the compositions of the invention are used in the prevention and treatment of caries. In such case, the reconstituted formula of the invention can be in the form of a varnish, which is easily applied over the tooth's surface, by means of a brush by a dentist, dental hygienist or other health care professional. Varnishes can be applied to the enamel, dentin, or cementum of the tooth as an adjunct to other forms of treatment. They are not permanent varnishes, but their adhesive consistency enables them to remain in contact with tooth surfaces for a period of several hours, enabling the colonization of the probiotic bacteria and providing the beneficial effects of the composition of the invention.

A preferred application procedure is explained hereinafter. Although it is not necessary to do a professional prophylaxis prior to the application of the solutions of the invention, it is recommended that the teeth are cleaned with a toothbrush and cleared of heavy plaque or debris if necessary. The teeth should be slightly dried with air or a cotton gauze. Teeth are isolated (e.g. with cotton rolls or absorbent material) to prevent recontamination with saliva. A small amount of varnish (e.g. 0.5 ml) is dispensed. The entire dentition may be treated with as little as 0.3-0.6 ml. The varnish will adhere even if the teeth are moist. A small brush or applicator is then used to apply the varnish. The patient is instructed to avoid brushing for the rest of the day. Normal oral hygiene procedures can begin again the following day.

In applications such as periodontitis, gingivitis, or caries, the compositions of the invention can also be applied by the patient itself. The commercial product can be a dental kit as described above comprising a brush for easy implementation.

In other embodiments, the compositions and kits of the invention are used by the dental professional in an acute treatment and the patient can follow a maintenance treatment with oral care products such as chewing gums, a toothpaste, a mouth wash, mouth spray, lozenges or oral dispersible tablets comprising the self-film-forming composition in powder form of the invention or the lactic acid bacteria with common excipients.

Other Uses and Product Forms

The invention also provides the self-film-forming composition in powder form or the reconstituted formula, for use in oral care, i.e. for non-medicament use. Therefore, the compositions of in the invention can be formulated in the form of mouthwashes, sprays, oral gels, and toothpastes, with the help of the conventional ingredients used for these oral forms, well known by those skilled in the art.

As known to those skilled in the art, mouthwashes are aqueous or water-alcohol solutions for rinsing the mouth which have a well-known, conventional formulation. In addition to water, polyhydroxylated compounds such as glycerine or glycols (e.g., propylene glycol, nonionic surfactants, etc.) and other additives to improve appearance, flavour, and preservation can be included.

The sprays are compositions equal or similar to mouthwashes but dispensed in spray bottles for convenient application of the dose needed to moisten and protect the mouth without requiring subsequent rinsing.

Oral gels include polymers which allows direct, stable application to the oral cavity. In relation to these polymers, for the purposes of this invention it is preferable to use a combination of polymers generically known as polycarbophil and carbomer, since they keep the gel structure stable for very prolonged times under extreme temperature conditions. The gels can also include a quantity of a natural, noncariogenic sweetener, such as sorbitol.

The formulation of toothpastes is well-known by those skilled in the art. In the toothpaste compositions, it is preferable to use nonionic (e.g. fatty acids esters with sugars) or amphoteric (e.g. coco-derived betaines) surfactants, since anionic surfactants have a negative effect on the delicate epithelial tissue of the gums. In the case of toothpastes, the use of sodium bicarbonate to neutralize oral acidity is also particularly preferred. In addition, toothpastes can contain thickening agents such as xanthan gum, abrasive silica fillers, and other supplementary agents in addition to those normally used in the toothpaste industry. Preferably, the lactic acid bacteria is encapsulated or protected in other form to be introduced in a toothpaste.

Lactic Acid Bacteria Strains

Other aspects of the invention relate with new strains of *Pediococcus* genus, especially beneficial for the prevention and treatment of peri-implantitis and other oral conditions related with oral dysbiosis. These new strains are the result of extensive studies of different lactic acid bacteria strains isolated from healthy humans. *Pediococcus pentosaceus* PERI1, *Pediococcus acidilactici* PERI2, *Pediococcus pentosaceus/acidilactici* PERI3, *Pediococcus pentosaceus/acidilactici* PERI4, were deposited on 16 Jun. 2015 in the Spanish Type Culture Collection (Colección Espanola de Cultivos Tipo, CECT, Edificio 3 CUE, Parc Cientific Universitat de Valencia, Catedrático Agustin Escardino, 9, 46980-Paterna, Valencia, Spain), by the depositor AB-Biotics, S.A., sited at Parc de Recerca UAB, Campus UAB, s/n Edifici Eureka, 08193 Cerdanyola del Valles (Barcelona, Spain). The strains received the accession numbers CECT 8903, CECT 8904, CECT 8905 and CECT 8906, respectively after the International Authority of Deposit declared the strains as viable.

The strains were selected because of the following distinguishing properties/capacities:

Good capacity to survive in the oral cavity as the strains tolerate well the presence of lysozyme and hydrogen peroxide, two bactericidal agents commonly present in the oral cavity.

The capacity to tolerate well and grow in the presence of a gelifier agent and/or a bioadhesive agent. For example, the growth of the selected strain in saliva is enhanced in the presence of the gelifier agent such as guar gum and/or the bioadhesive agent such as hydroxyethylcellulose.

The capacity to inhibit the growth of oral pathogens. For instance, the strains are able to antagonize bacteria associated with peri-implantitis including *Fusobacterium nucleatum, Porphyromonas gingivalis, Prevotella intermedia* and/or *Aggregatibacter actinomycetemcomitans*.

Capacity to aggregate, which is a requirement for forming a biofilm that can have a protective effect against the colonization of other pathogens by forming a natural barrier.

A wide variety of lactic acid bacterial species have a long history of apparent safe use. The European Food Safety Authority has developed a system granting the "Qualified Presumption of Safety" (QPS) status to taxonomical units with a proven long history of apparent safe use. The strains of the invention belong to bacterial species that have QPS status [Andreoletti, O. et al. 2008].

In summary, it is believed that no prior art describes *Pediococcus* strains and particularly *Pediococcus acidilactici* and *Pediococcus pentosaceus* strains with the above-mentioned features and for use in the prevention and/or treatment of peri-implantitis. It is noteworthy that the strains *Pediococcus* CECT 8903, *Pediococcus* CECT 8904, *Pediococcus* CECT 8905, *Pediococcus* CECT 8906, meet all the previously mentioned properties together, being therefore suitable for treating peri-implantitis.

In a particular embodiment, the isolated strain has been fermented in an artificial medium and submitted to a post-treatment after the fermentation, to obtain bacterial cells, and the resulting bacterial cells are in a liquid medium or in a solid form. Particularly, the post-treatment is selected from the group consisting of: drying, freezing, freeze-drying, fluid bed-drying, spray-drying and refrigerating in liquid medium, and more particularly, is freeze-drying.

The strains of the invention are produced by cultivating (or fermenting) the bacteria in a suitable artificial medium and under suitable conditions. By the expression "artificial medium" for microorganisms is to be understood a medium containing natural substances, and optionally synthetic chemicals such as the polymer polyvinyl alcohol which can reproduce some of the functions of serums. Common suitable artificial media are nutrient broths that contain the elements including a carbon source (e.g. glucose), a nitrogen source (e.g. amino acids and proteins), water and salts needed for bacterial growth. Growth media can be liquid form or often mixed with agar or other gelling agent to obtain a solid medium. The strains can be cultivated alone to form a pure culture, or as a mixed culture together with other microorganisms, or by cultivating bacteria of different types separately and then combining them in the desired proportions. After cultivation, and depending on the final formulation, the strains may be used as purified bacteria, or alternatively, the bacterial culture or the cell suspension may be used, either as such or after an appropriate post-treatment. In this description, the term "biomass" is understood the bacterial strains culture obtained after cultivation (or fermentation as a term synonymous to cultivation).

By the term "post-treatment" is to be understood in the context of the present invention, any processing carried out on the biomass with the aim of obtaining storable bacterial cells. The objective of the post-treatment is decreasing the metabolic activity of the cells in the biomass, and thus, slowing the rate of cellular deleterious reactions. As a result of the post-treatment, the bacterial cells can be in solid or liquid form. In solid form, the stored bacterial cells can be a powder or granules. In any case, both the solid and liquid forms containing the bacterial cells are not present in the nature, hence, are not naturally-occurring, since they are the result of artificial post-treatment process(es). The post-treatment processes may in particular embodiments require the use of one or more of so-called post-treatment agent. In the context of the present invention, the expression "post-treatment agent" refers to a compound used to perform the herein described post-treatment processes. Among the post-treatment agents are to be included, without limitation, dehydrating agents, bacteriostatic agents, cryoprotective agents (cryoprotectants), inert fillers (also known as lyoprotectants), carrier material (also known as core material), etc., either used alone or in combination.

There are two basic approaches to decrease the metabolic activity of the bacterial cells, and thus, two approaches to carry out the post-treatment. The first one is decreasing the rate of all chemical reactions, which can be done lowering the temperature by refrigerating or freezing using refrigerators, mechanical freezers, and liquid nitrogen freezers. Alternatively, decreasing the rate of all chemical reactions can be achieved by adding substances that inhibit the growth of the bacterial cells, namely a bacteriostatic agent, abbreviated Bstatic.

The second approach to carry out the post-treatment is to remove water from the biomass, a process which can involve sublimation of water using a lyophilizer. Suitable techniques to remove water from the biomass are drying, freeze-drying, spray-drying or fluid bed-drying. Post-treatments that result in solid form may be drying, freezing, freeze-drying, fluid bed-drying, or spray-drying.

The post-treatment is preferably freeze-drying, which involves the removal of water from frozen bacterial suspensions by sublimation under reduced pressure.

This process consists of three steps: pre-freezing the product to form a frozen structure, primary drying to remove most water, and secondary drying to remove bound water. Due to objective and expected variability of industrial processes for manufacturing and isolation of lyophilized bacterial cultures, the latter commonly contain certain amount of inert filler also known as lyoprotectant. Its role is to standardize the content of live probiotic bacteria in the product. The following inert fillers in commercially available lyophilized cultures are used: sucrose, saccharose, lactose, trehalose, glucose, maltose, maltodextrin, corn starch, inulin, and other pharmaceutically acceptable non-hygroscopic fillers. Optionally, other stabilizing or freeze-protecting agents like ascorbic acid, are also used to form a viscous paste, which is submitted to freeze-drying. In any case, the so-obtained material can be grinded to appropriate size, including to a powder.

It is clear that by using the deposited strains as starting material, the skilled person in the art can routinely, by conventional mutagenesis or re-isolation techniques, obtain further mutants thereof that retain or enhance the herein described relevant features and advantages of the strains forming the composition of the invention. In one particular embodiment, the mutants are obtained by using recombinant DNA technology. In another embodiment, the mutants are obtained by random mutagenesis. Thus, another aspect of the invention relates to a method to obtain a mutant of at least one strain of *Pediococcus*, wherein the strain is selected from the group consisting of: strain CECT 8903, strain CECT 8904, strain CECT 8905, and strain CECT 8906, wherein the method comprises using the deposited strain as starting material and applying mutagenesis, and wherein the obtained mutant further retains or enhances at least the ability of the deposited strain to antagonize at least one oral pathogen selected from the group consisting of bacteria of the genus: *Porphyromonas, Fusobacterium, Prevotella*, and *Aggregatibacter*.

Additional aspects of the invention are a pharmaceutical product, a veterinary product, a medical food, a food product, a food supplement and an oral care product, comprising an effective amount of at least one of the strains as defined above, together with appropriate amounts of acceptable excipients.

Selection of the excipients and the most appropriate methods for formulation in view of the particular purpose of the composition is within the scope of ordinary persons skilled in the art of pharmaceutical technology. The strains of the invention can be formulated in a form in which they are the only active agent or mixed with one or more other active agents.

The term "excipient" is understood in its widely meaning in this description, including any natural or synthetic substance formulated alongside the active ingredient of a pharmaceutical product, veterinary product, a medicament, food supplement, medical food and oral care product. Excipients are selected, without limitation, from the group comprising: fillers/diluents/bulking agents, binders, antiadherents, disintegrants, coatings, anti-caking agents (e.g. magnesium stearate, colloidal silicon dioxide, or talc), antioxidants, lubricants, sweeteners, flavors, colors, tensides and other classes of pharmaceutically and veterinary acceptable excipients.

The effective amount of colony forming units (cfu) for the strains in the composition will be determined by the skilled in the art and will depend upon the final formulation. For instance, when administered orally without any other active agent, the total amount of the strains of the invention is present in the composition in single doses in amount giving an effective daily dose of from $10^7$ to $10^{12}$ cfu, according to the current legislation, preferably from $10^9$ to $10^{11}$ cfu. The term "colony forming unit" ("cfu") is defined as number of bacterial cells as revealed by microbiological counts on agar plates. Food supplements usually contain probiotic strains in an amount ranging from $10^7$ and $10^{12}$ cfu/g.

The term "pharmaceutical product" is understood in its widely meaning in this description, including any composition that comprises an active ingredient, in this case, the strains of the invention preferably in form of composition, together with pharmaceutically acceptable excipients. This term is not limited to medicaments. The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The pharmaceutical product can adopt different forms or names depending on the product approval route and also depending on the country. For instance, a medicament is a particular pharmaceutical product. A medical food is another particular pharmaceutical product. The terms "medical food" or "food for special medical purposes" are used in some countries to refer to a food specially formulated and intended for the dietary management of a disease that has distinctive nutritional needs that cannot be met by normal diet alone. They are defined in regulations such as the Food and Drug Administration's 1988 Orphan Drug Act Amendments in the United States, and the Commission Directive 1999/21/EC in Europe. Medical foods are distinct from the broader category of food supplements and from traditional foods that bear a health claim. Thus, in a particular embodiment, the strains of the invention are formulated as a medical food.

Often, probiotic bacterial compositions such as the one disclosed herein, are considered as food supplements. A food supplement, also known as dietary supplement or nutritional supplement is considered another particular pharmaceutical product. This is a preparation or product intended to supplement the diet, made from compounds usually used in foodstuffs, which provide nutrients or beneficial ingredients that are not usually ingested in the normal diet or may not be consumed in sufficient quantities. Mostly, food supplements are considered as food products, but sometimes they are defined as drugs, natural health products, or nutraceutical products. In the sense of the present invention, food supplements also include nutraceuticals. Food supplements are usually sold "over the counter", i.e. without prescription. If the food supplement adopts the form of a pill, a capsule a tablet or a powder, it comprises excipients which are the same as the used in medicaments. A food supplement however, can also adopt the form of a food product which is fortified with some nutrients (e.g. a bar or yoghurt). Thus, in a particular embodiment, the strains of the invention are formulated as a food supplement. The food supplement can be administered as such, can be mixed with a suitable drinkable liquid, such as water, yoghurt, milk or fruit juice, or can be mixed with solid or liquid food. In this context the food supplement can be in the form of tablets or lozenges, pills, capsules, granules, powders, suspensions, sachets, sweets, bars, syrups and corresponding administration forms, usually in the form of a unit dose.

The strains of the invention can be also included in a variety of food products, such as a milk products (a yogurt, a cheese, a fermented milk, a milk powder, a milk based fermented product, an ice-cream, a fermented cereal based product, a milk based powder), bread, bars, spreads, biscuits and cereals, a beverage, different types of oil, or a dressing. The term "food product" is used herein in its broadest meaning, including any type of product, in any form of presentation, which can be ingested by an animal, but excluding pharmaceutical and veterinary products. Examples of other food products are meat products, chocolate spreads, fillings and frostings, chocolate, confectionery, baked goods, sauces and soups, fruit juices and coffee whiteners. Particularly interesting food products are food supplements and infant formulas. The food product preferably comprises a carrier material such as oat meal gruel, lactic acid fermented foods, resistant starch, dietary fibres, carbohydrates, proteins and glycosylated proteins. In a particular embodiment the strains of the invention are encapsulated or coated.

The compositions of the invention are meant for use in oral health applications. Accordingly, another aspect of the present invention provides an oral care product comprising the composition as mentioned above, together with pharmaceutically excipients, or cosmetically acceptable excipients, or other edible ingredients. In this sense, the composition is an oral product that is not intentionally swallowed for systemic administration of particular therapeutic agents, but instead is retained in the oral cavity for a time sufficient to contact substantially all of the dental surfaces and/or oral tissues for purposes of oral activity. Non limiting examples of such products are toothpastes, dentifrices, tooth powders, topical oral gels, mouth rinses, denture products, mouth sprays, chewing gums, dental floss, dental tapes, blasting powder, polishing pastes, dental varnishes, fissure sealants, filling materials, oral cream or gel, candy, lozenges, oral dispersible tablet or strip, or powder that may be sprinkled directly into the oral cavity. The oral care products may additionally comprise flavoring compounds such as menthol.

Embodiments described above apply in the area of treatment, therapy and prophylaxis also in veterinary medicine, in particular, in dogs, cats, cattle, horses, monkeys, sheep, goats. Particular articles for animals are those for chewing, biting and gnawing, sticks, animal snacks, pet food, pellets, or pet toys.

Thus, it has to be understood that the strains of the invention are useful in the management of oral dysbiosis regardless of the form of the composition; i.e. regardless of being a pharmaceutical product, a medicament, a food product, a food supplement, a medical food, or an oral care product.

Another aspect of the present invention relates to a solid composition comprising a cryoprotectant; a freeze-dried biomass comprising at least one lactic acid bacteria; and a pharmaceutically acceptable carrier. The pharmaceutically acceptable carrier preferably is chosen from an emulsion, a gel, a paste, granules, a powder, and a gum. Additional aspects of the invention provide an oral care product, a pharmaceutical composition, and edible product, a dietary supplement and a cosmetic composition comprising an effective amount of the composition as defined in the previous aspect. In a particular embodiment, the oral care product is a chewing gum, a tooth paste, a mouth spray, a lozenge, or an oral dispersible tablet. In a particular embodiment, the pharmaceutical composition, the edible product or the dietary supplement, is a lozenge or an oral dispersible tablet.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. Furthermore, the present invention covers all possible combinations of particular and preferred embodiments described herein.

The following examples and drawings are provided herein for illustrative purposes, and without intending to be limiting to the present invention.

EXAMPLES

Example 1. Isolation of the Microorganisms

Lactic acid bacteria candidates were isolated from fresh stools and oral hyssops from 0-9 year-old children. Samples were dissolved in PBS buffer (pH 7.4), aliquoted and plated on MRS supplemented with various antibiotic combinations. Strains were cultured under microaerophilic conditions (5% $CO_2$) at 37 or 30° C. Incubation time depended on the growth rate, but ran normally from 24 hours to 3 days. Isolation of individual strains proceeded with the same selection media, and then Gram staining was carried out in order to get a first identification. Once grown, isolated strains were stored by freeze-drying in PBS 0.1× with 15% skim milk powder.

Example 2. Genus and Species Identification

Identification to species level was performed by sequencing 16S rRNA gene. Briefly, the DNA of the strains was extracted with Chelex® 100 resin from Bio-Rad Laboratories (Barcelona, Spain). Complete sequence of 16S rRNA gene was amplified by polymerase chain reaction (PCR) using the universal primers for eubacteria 27F and 1492R as previously described [Weisburg, W. G. et al. 1991; Muyzer, G. et al. 1998]. The integrity of PCR products was checked in an agarose gel using SYBR green dye (Invitrogen, Life Technologies, Madrid, Spain). PCR products were sequenced using 27F, 357F, 907R and 1492 primers [Weisburg, W. G. et al. supra; Muyzer, G. et al. supra], a v3.1 Cycle Sequencing kit and an 3130 XL Genetic Analyzer (from Applied Biosystems, Life Technologies, Madrid, Spain). The resulting sequences were aligned and compared with those presents in the National Center for Biotechnology Information (NCBI) and RDP (Ribosomal Database Project). The strains were identified based on the highest hit scores.

The 16S rRNA sequences corresponded to the *Pediococcus* genus. When compared with NCBI and RDP databases, the sequence of PERI1 corresponded to *P. pentosaceus* (100% identity); the sequence of PERI2 corresponded to *P. acidilactici* (100%); the sequence of PERI3 corresponded with a 100% of identity to either *P. pentosaceus* or *P. acidilactici*; and the sequence of PERI4 corresponded with a 99% of identity to either *P. pentosaceus* or *P. acidilactici*. They were deposited in the Spanish Type Culture Collection (CECT) under the accession numbers CECT 8903, CECT 8904, CECT 8905 and CECT 8906, respectively.

Example 3. Strain Genotyping

Figure 6:
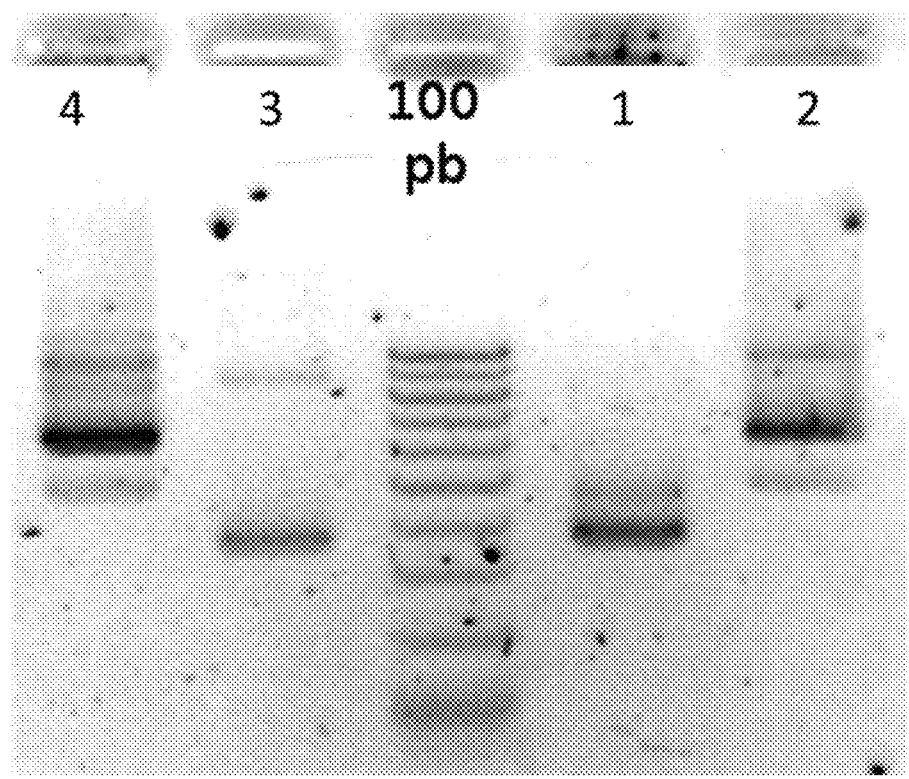
FIG. 6: Strain genotyping by random amplified polymorphic DNA (RAPD). Patterns obtained after random amplification for 1, PERI1; 2, PERI2; 3, PERI3; 4, PERI4.

Strain genotyping was performed by random amplified polymorphic DNA (RAPD) for confirming that the four strains of *Pediococcus* sp. deposited were different between them. RAPD was performed as described by Nigatu et al. 1998. RAPD patterns of the strains are depicted in FIG. 6, demonstrating that the four strains were different.

Example 4: Survival to Oral Conditions

Survival of the strains in the oral cavity was studied by evaluating their tolerance to different concentrations agents known to compromise bacterial survival such as hydrogen peroxide (HP) and lysozyme. A total number of 50 lactic acid bacteria candidates were evaluated and compared with commercial probiotics strains namely *Streptococcus salivarius* K12 (Blis Technologies, New Zeland) and *Lactobacillus reuteri* DSM17938 (Biogaia, Sweden) which were used as controls.

Probiotic candidates and *L. reuteri* DSM17938 were grown in Man Rogosa Sharpe agar medium (MRSa) for 18-24 hours at 37° C. and microaerophilic conditions (5% of $CO_2$). *S. salivarius* K12 was grown under the same conditions but using Brain Hearth Infusion medium (BHI) instead of MRS. Isolated colonies were used for preparing a bacterial suspension in 0.1 M Phosphate Buffered Saline (PBS) with an optical density corresponding to a McFarland standard 0.5 (approximately 1E+08 CFU/mL). Bacterial suspensions were subsequently 2-fold diluted in MRS or BHI liquid media. Microplates of 96 wells were inoculated with two-hundred microliters of the resulting dilution to which 50 µl of a solution containing either lysozyme or HP in PBS were added. The concentrations of lysozyme tested were $1\times10^6$ and $5\times10^6$ U/mL (final concentration in the well of $2\times10^5$ and $1\times10^6$ U/mL, respectively) and the concentrations of HP were 5 mM and 25 mM (final concentration in the well of 1 mM and 5 mM, respectively). Microwell plates were incubated for 6 h at 37° C. in microaerophilic conditions (5% of $CO_2$). Bacterial growth was monitored by determining the absorbance at 625 nm. Percentage of growth was calculated comparing the increment observed in the presence of lysozyme or HP compared to the growth of the bacterial strain in the absence of these agents (positive control) using the following formula:

$$\text{Growth } (\%) = \frac{OD_{LH} - OD_{C-}}{OD_{C+} - OD_{C-}} * 100$$

wherein $OD_{LH}$ was the optical density of the well containing microorganism and either lysozyme or HP,
$OD_{C-}$ was the average optical density of three wells with the same amount of lysozyme without microorganism,
$OD_{C+}$ was the average optical density of the three wells inoculated with bacteria but not lysozyme nor HP (positive control).

Results:

Seven of the fifty probiotic candidates did not grow even in control MRS media (not supplemented). Thus, these strains were discarded as potential candidates. The remaining 43 were ranked according to their capacity to grow in the presence of the highest concentration of lysozyme and HP tested. Results are shown in TABLE 1 and are expressed as means of survival in percentage compared to the growth of the same strain in media not supplemented with lysozyme nor HP.

TABLE 1

Tolerance of bacteria to lysozyme and hydrogen peroxide concentrations.

|  | Lysozyme (2E+5 U/mL) | Lysozyme (1E+6 U/mL) | HP (1 mM) | HP (5 mM) |
|---|---|---|---|---|
| PERI3 | n.i. | n.i. | n.i. | n.i. |
| F2043 | n.i. | n.i. | n.i. | n.i. |
| F2002A | n.i. | n.i. | n.i. | n.i. |
| PERI1 | n.i. | n.i. | n.i. | n.i. |
| I1003 | n.i. | n.i. | n.i. | n.i. |
| I3153 | 92.1 | n.i. | n.i. | 90.8 |
| *L. reuteri* DSM17938 | n.i. | n.i. | 87.9 | 53.4 |
| I3145 | n.i. | n.i. | n.i. | n.i. |
| F3163 | 98.7 | n.i. | n.i. | n.i. |

TABLE 1-continued

Tolerance of bacteria to lysozyme and hydrogen peroxide concentrations.

| | Lysozyme (2E+5 U/mL) | Lysozyme (1E+6 U/mL) | HP (1 mM) | HP (5 mM) |
|---|---|---|---|---|
| F1031 | 84.5 | n.i. | 91.7 | 92.3 |
| F2003A | n.i. | n.i. | n.i. | n.i. |
| PERI4 | n.i. | n.i. | n.i. | n.i. |
| I3028 | 93.0 | n.i. | 86.0 | 86.0 |
| I1005 | n.i. | n.i. | n.i. | n.i. |
| F2008A | 99.8 | n.i. | n.i. | n.i. |
| F2006 | n.i. | n.i. | n.i. | n.i. |
| I3118 | 89.6 | 99.1 | 92.5 | 90.5 |
| F3166 | n.i. | 97.8 | n.i. | n.i. |
| PERI2 | 89.2 | 96.9 | n.i. | 92.4 |
| I3143 | 93.5 | 96.9 | 90.9 | 84.9 |
| I3030 | 91.3 | 92.0 | 92.0 | 92.8 |
| I3061 | 92.8 | 91.6 | 93.4 | 90.0 |
| I3149 | n.i. | 90.6 | n.i. | n.i. |
| I3142 | 93.8 | 90.3 | 98.1 | 96.8 |
| I3140 | 89.8 | 87.0 | 93.3 | 93.8 |
| L. salivarius K12 | 99.9 | 86.7 | 92.9 | 80.5 |
| I3142A | n.i. | 86.4 | n.i. | 90.4 |
| I3130 | 91 | 84.1 | 90.2 | 88.3 |
| I1004 | 90.9 | 83.3 | 106.0 | 96.5 |
| F2002B | 80.7 | 81.0 | n.i. | n.i. |
| F2008B | 72.4 | 76.7 | n.i. | n.i. |
| F3162 | 86.0 | 63.2 | 95.7 | n.i. |
| F2009 | 85.4 | 62.3 | n.i. | n.i. |
| I3142B | 94.7 | 59.1 | n.i. | n.i. |
| F2005 | 85.2 | 58.2 | n.i. | n.i. |
| F3164 | 94.5 | 46.3 | n.i. | n.i. |
| I1002 | 31.5 | 40.4 | n.i. | 95.7 |
| I3096 | 41.9 | 38.3 | 90.4 | 87.9 |
| F2041 | 36.9 | 29.3 | n.i. | n.i. |
| F2044 | 34.8 | 25.1 | n.i. | n.i. |
| F2003B | 31.7 | 13.4 | n.i. | n.i. |
| F3165 | n.i. | 11.8 | n.i. | n.i. |
| I3086 | 87.1 | 10.9 | 87.2 | 87.0 |
| F3159B | n.i. | 5.0 | n.i. | n.i. |

Abbreviations: n.i. = no inhibition (growth 100%); HP = hydrogen peroxide.

The 25 first bacteria showing the highest tolerance to lysozyme and HP were considered the best candidates and were selected for subsequent in vitro test for evaluating their probiotic properties. As can be observed all the strains showed good tolerance to high concentrations of lysozyme showing a survival ratio not lower than 86%, which was similar to that of the commercial controls. The LAB candidates showed also good tolerance to HP with values higher than 84% at a concentration of 5 mM of HP. These results compared well with the survival ratio of the commercial controls L. reuteri DSM17938 and L. salivarius K12 (53.4 and 80.5% respectively).

Example 5: Use of Guar Gum as a Gelifier with Prebiotic Effect

The capacity of the strains to use guar gum and increase their growth was studied in vitro. For this purpose, the growth of probiotic candidates in artificial saliva supplemented with guar gum was compared to their respective growth in artificial saliva that was not supplemented. Artificial saliva contained 1 g/L 'Lab-lemco' powder (Oxoid, Basingstoke, UK), 2 g/L yeast extract (Oxoid), 5 g/L proteose peptone (Oxoid), 2.5 g/L hog gastric mucin (Sigma Chemical Co., Poole, UK), 35 g/L sodium chloride (BDH Chemicals Ltd, Poole, UK), 0.2 g/L calcium chloride (BDH), 0.2 g/L potassium chloride (BDH) in distilled water. Artificial saliva was supplemented with guar gum (Genox Pharma, Barcelona, Spain) to a final concentration of 0.5% (w/v). Artificial saliva without gel ingredient was also prepared to compare the effect of guar gum in bacterial growth with a non-supplemented medium. After autoclaving, 1.25 mL of 40% urea per liter of artificial salivary medium were added. Two hundred microliters of the different media prepared were pipetted in 96-well plates. Immediately after 20 microliters of a suspension of probiotic candidates standardized to 1E+07 CFU/mL in PBS were added. The same amount of PBS without bacterial inoculum was used as a negative control. Plates were incubated for 24 h at 37° C. in anaerobiosis and bacterial growth monitored by determining the optical density at 625 nm. The capacity of probiotic candidates to use guar gum for growing was calculated according to the following formula:

$$\Delta Growth = (\Delta DO_{gp} - \Delta DO_{g0}) - (\Delta DO_{sp} - \Delta DO_{s0})$$

wherein $\Delta DO_{gp}$ is the difference between the optical density at 625 nm after 24 h compared with 0 h in the wells supplemented with guar gum and inoculated with probiotic candidates;

$\Delta DO_{g0}$ is the difference between the optical density at 625 nm at 24 h compared with 0 h in the wells supplemented with guar gum but containing PBS instead of LAB;

$\Delta DO_{sp}$ is the difference between the optical density at 625 nm at 24 h compared with 0 h in the wells not supplemented with guar gum and inoculated with probiotic candidates; and $\Delta DO_{s0}$ is the difference between the optical density at 625 nm at 24 h compared with 0 h in the wells not supplemented with guar gum and containing PBS instead of LAB.

Results were compared with those obtained with the commercial probiotics L. reuteri DSM 17938, L. brevis CD2, Streptococcus salivarius K12 and with the pathogens Fusobacterium nucleatum and Porphyromonas gingivalis. The experiment was performed in duplicate.

Results

Figure 1:
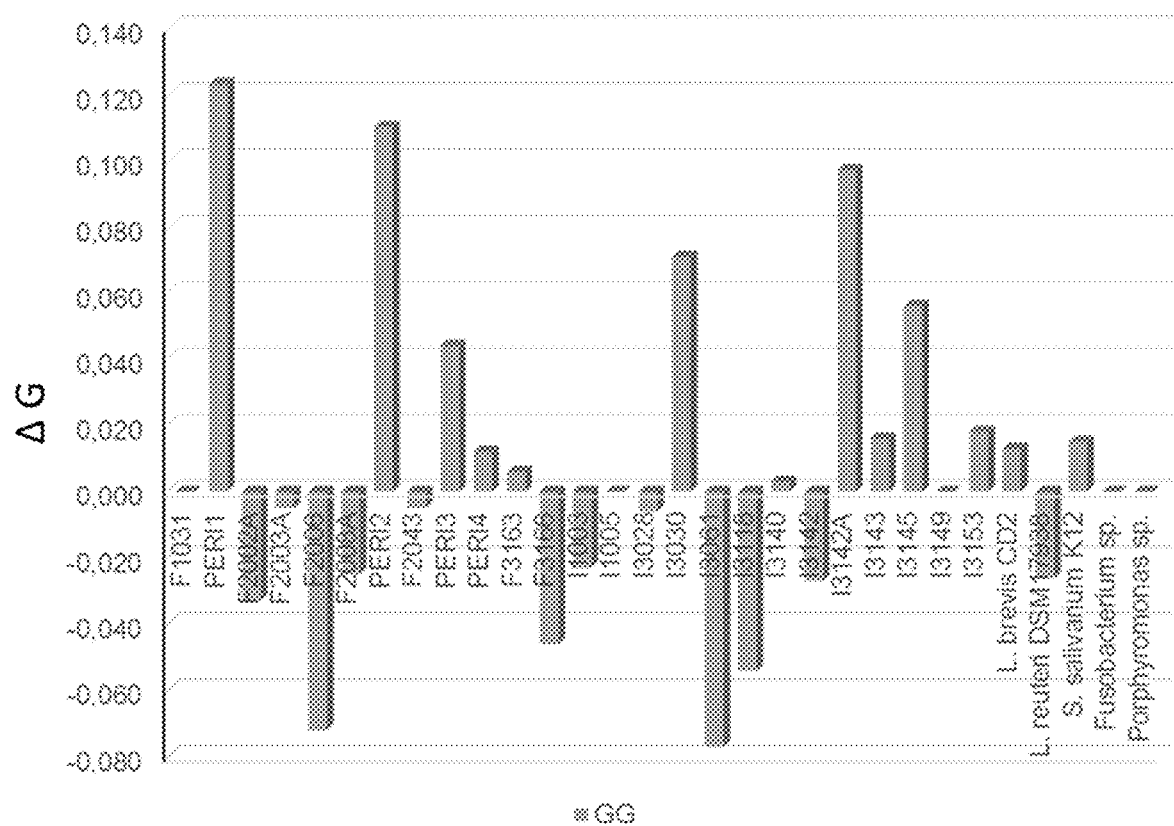
FIG. 1: Growth (G) of probiotic strains in artificial saliva supplemented with guar gum (GG) compared to non-supplemented artificial saliva.

The capacity to use guar gum as a nutrient and potentiate their growth compared to non-supplemented artificial saliva is depicted in FIG. 1. The effect of guar gum on LAB growth was highly dependent on the strain tested. Whereas guar gum potentiated the growth of some strains, it had a detrimental effect in the growth of others compared to non-supplemented saliva. The strains PERI1; PERI2; PERI3; PERI4; F3163; I1003; I1005; I3028; I3030; I3140; I3142A; I3145 and I3153 benefit from the addition of guar gum. PERI1 was the strain showing the highest performance. Among the control strains tested, L. brevis CD2 and S. salivarius K12 benefit from the addition of guar gum, although the effect of guar gum on the growth of this strains was lower than other LAB candidates such as PERI1, PERI2, PERI3, F3163; I1003 and 3142A. Notably, the effect of guar gum was negligible in the case of Fusobacterium nucleatum and Porphyromonas gingivalis which is of interest for avoiding the undesirable growth of pathogens.

Example 6: Use of Hydroxyethylcellulose (HEC) as an Adhesive Agent with Prebiotic Effect The capacity of the strains to use HEC to potentiate their growth was assayed as explained above in Example 5 for guar gum.

Results

Figure 2:
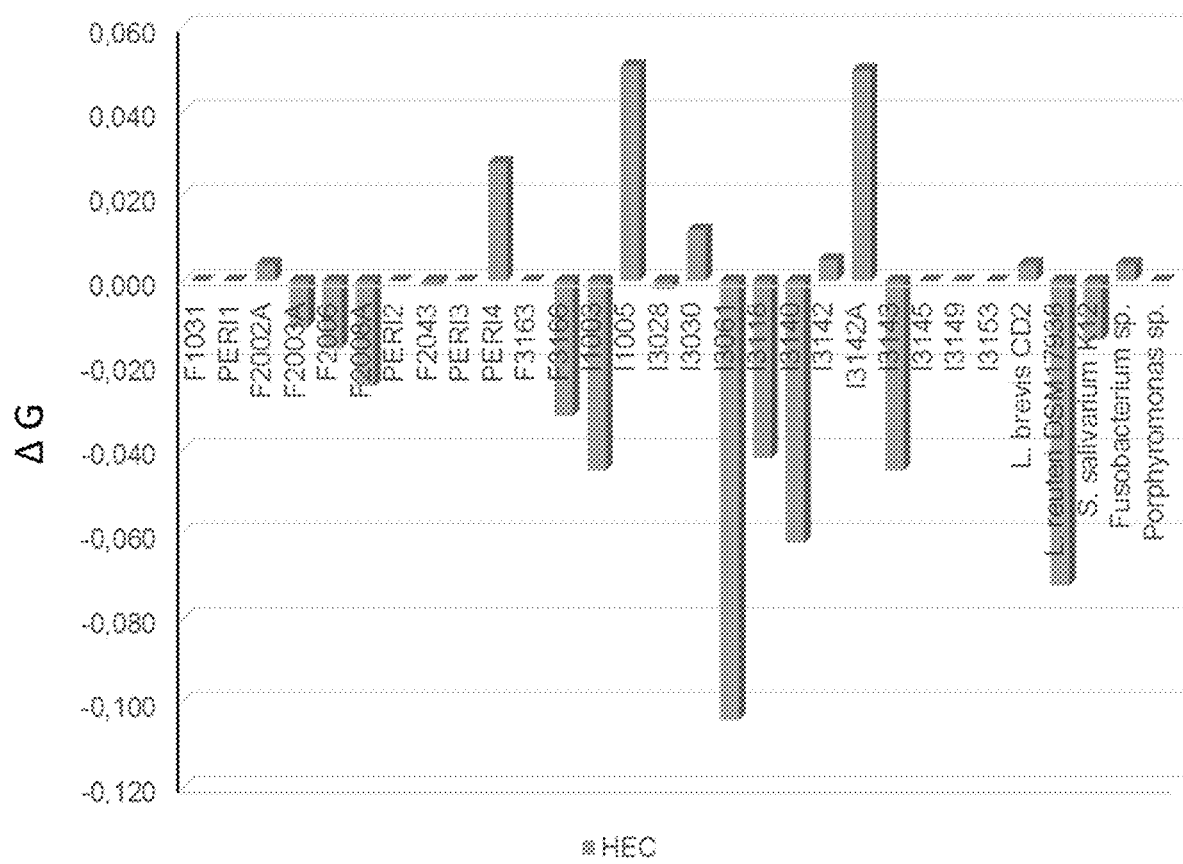
FIG. 2: Growth (G) of probiotic strains in artificial saliva supplemented with hydroxyethylcellulose (HEC) compared to non-supplemented artificial saliva.

The effect of HEC on probiotic growth compared to non-artificial saliva is shown in FIG. 2. The growth of few strains was potentiated by the addition of HEC. Strains namely PERI4, I1005 and I3142A were significantly benefited by the use of HEC in the gel. Other strains, including the commercial strains had low capacity to use this ingredient.

Example 7: Use of Other Gelifier Agents as Ingredient with Prebiotic Effect

The potential use of other gelifier agents to increase probiotic growth was also studied by using the same methodology explained above. Particularly, sodium alginate (SA) and methylcellulose (MC) were used as potential gelifier agents with prebiotic effect.

Results

Figure 3:
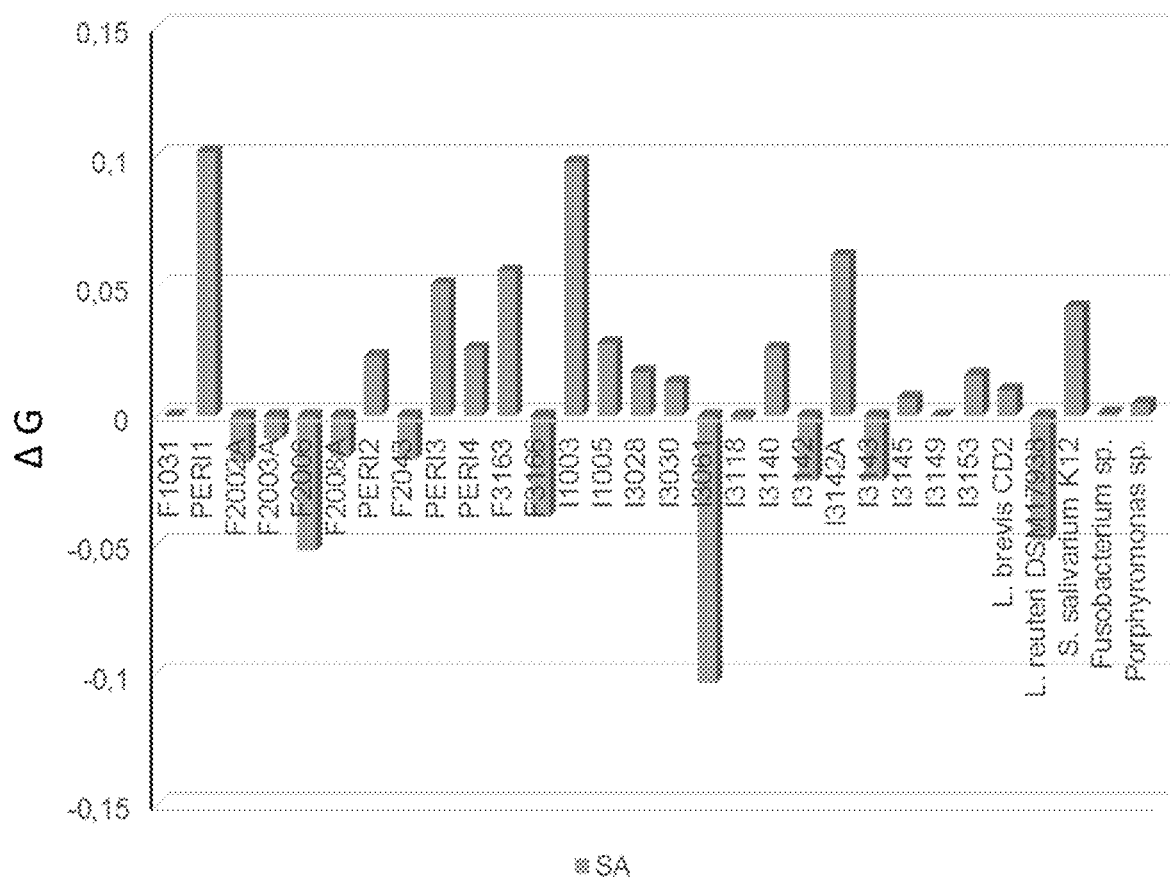
FIG. 3: Growth (G) of probiotic strains in artificial saliva supplemented with sodium alginate (SA) compared to non-supplemented artificial saliva.
Figure 4:
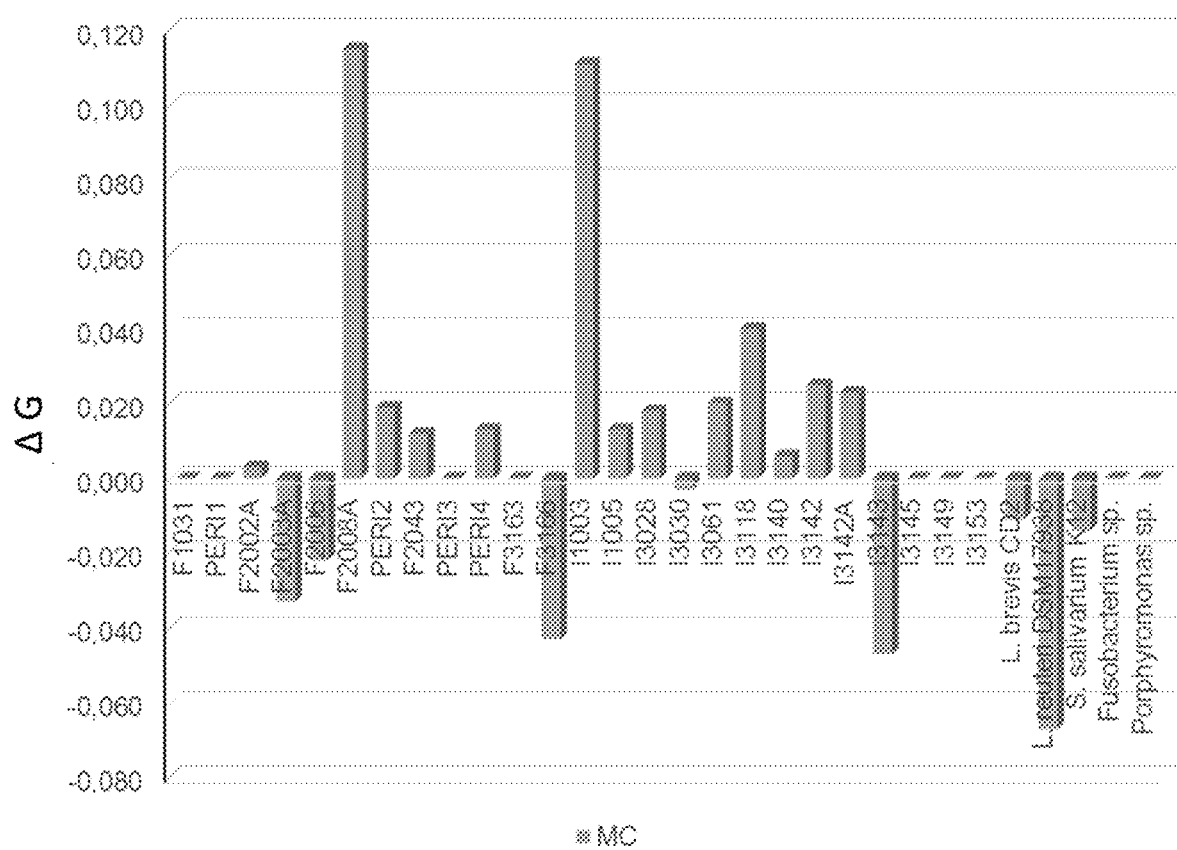
FIG. 4: Growth (G) of probiotic strains in artificial saliva supplemented with methylcellulose (MC) compared to non-supplemented artificial saliva.

The effect of SA supplementation on bacterial growth compared to non-supplemented artificial saliva is depicted in FIG. 3. Different strains were able to use SA as nutrient for increasing their growth including PERI; PERI2; PERI3; PERI4; I1003; I1005; I3028; I3030; I3130; I3142A; I3145 and I3153. In contrast, *Fusobacterium nucleatum* and *Porphyromonas gingivalis* had low capacity to use SA for growing. Results for MC are present in FIG. 4. None of the pathogen and control strains were able to use MC for increasing growth. In contrast, different probiotics strains benefit from the supplementation of MC, including F2008A; PERI2; F2043; PERI4; I1003; I1005; I3028; I3061; I3118; I3140 and I3142A.

Example 8: Antagonism Against *Porphyromonas gingivalis, Fusobacterium nucleatum* and *Prevotella intermedia*

The antagonistic activity of probiotic candidates was assessed against bacteria abnormally abundant in patients presenting peri-implantitis. In particular, the pathogen strains were *Porphyromonas gingivalis* DSM-20709, *Fusobacterium nucleatum* DSM 20482 and *Prevotella intermedia* DSM-20706 DSM 8324. *L. reuteri* DSM 17938 from Biogaia (Sweden), *L. brevis* CD2 (Inersan®, VSL Pharmaceuticals, Inc., USA) and *Streptococcus salivarius* K12 (BLIS Technologies, New Zealand) were used as commercial controls. The capacity of the LAB candidates to inhibit pathogen growth was determined by using the Campbell protocol. Briefly, probiotic candidates and *Lactobacillus* controls were uniformly seeded in MRS agar plates and allowed to grow to confluence for 24 h at 37° C. and 5% of $CO_2$. *Streptococcus salivarius* K12 was grown under the same conditions but using BHI medium.

Pathogen strains were cultured overnight. Isolated colonies of these pathogens were used to prepare suspensions in phosphate buffered saline (PBS) medium and swabbed uniformly in appropriate solid medium for their growth: *F. nucleatum* and *P. intermedia* were seeded in blood agar and *Porphyromonas gingivalis* in Schaeder Anaerobe Sheep Blood Agar. Immediately, cylindrical sections of 6 mm in diameter of the confluent agar plate of the tested LAB candidates were placed lane-to-lane on the pathogen seeded plate, confronting the pathogen seeded plate with the grown-agar side of one of the cylinder sections and with the non-grown side of the other cylinder section. Plates were incubated 48 h at 37° C. in anaerobic conditions. Then, inhibition zones were measured by placing the agar plate over a flat rule and measuring the halos where pathogen growth was inhibited (either partially or completely). Growth inhibitory activity (GI) was then calculated by subtracting the cylinder diameter (CD) from the inhibition zone diameter (IZD) measured in millimeters. The final inhibitory activity was calculated as a mean value of the GI values for the two above-mentioned cylinder sections for each probiotic strain, i.e. averaging the duplicates. All experiments were performed in duplicate.

Results

The antagonistic activity of the different probiotic candidates is detailed in TABLE 2. The strains PERI3, PERI4 and F3166 were the three strains showing the greatest activity against *F. nucleatum*, and showed a higher activity than *L. brevis* CD2, *L. reuteri* DSM17938 and *S. salivarius* K12. The candidates F1031 and PERI2 were the candidates showing the highest activity against *P. intermedia*. Several strains were also efficient inhibiting *P. gingivalis*. Among them PERI1, F2006, PERI2, F3163, I1003, I3143, I3145 and I3153 showed higher activity than the commercial controls used for comparison purposes.

TABLE 2

Inhibitory activity against *F. nucleatum, P. intermedia* and *P. gingivalis* (results expressed as means ± SD in mm)

| Strain | Fusobacterium nucleatum | Prevotella intermedia | Porphyromonas gingivalis |
|---|---|---|---|
| F1031 | n.i | 4.5 ± 0.7 | 3.5 ± 0.7 |
| PERI1 | 1.5 ± 0.7 | 2.0 ± 1.4 | 15.0 ± 1.4 |
| F2002A | 3.0 ± 0.0 | 1.0 ± 0.0 | n.i |
| F2003A | 1.5 ± 0.7 | n.i | n.i |
| F2006 | 2.0 ± 1.4 | n.i | 17.5 ± 0.7 |
| F2008A | 3.5 ± 0.7 | 1.0 ± 0.0 | 11.5 ± 0.7 |
| PERI2 | 2.0 ± 0.0 | 5.0 ± 0.0 | 13.5 ± 0.7 |
| F2043 | 3.5 ± 0.7 | n.i | n.i |
| PERI3 | 4.0 ± 1.4 | n.i | 14.0 ± 0.0 |
| PERI4 | 4.0 ± 0.0 | n.i | 11.0 ± 1.4 |
| F3163 | 2.0 ± 0.0 | 2.0 ± 2.8 | 13.0 ± 1.4 |
| F3166 | 4.0 ± 0.0 | n.i | n.i |
| I1003 | 0.5 ± 0.7 | 0.5 ± 0.7 | 16.0 ± 0.0 |
| I1005 | 1.0 ± 0.0 | n.i | n.i |
| I3028 | 3.0 ± 0.0 | n.i | n.i |
| I3030 | 2.5 ± 0.7 | n.i | n.i |
| I3061 | n.i | n.i | 8.0 ± 0.0 |
| I3118 | 2.0 ± 0.0 | n.i | n.i |
| I3140 | 1.5 ± 0.7 | n.i | 9.0 ± 1.4 |
| I3142 | 1.5 ± 0.7 | 1.0 ± 0.0 | 8.0 ± 1.4 |
| I3142A | n.i | 0.5 ± 0.7 | n.i |
| I3143 | 2.5 ± 0.7 | n.i | 13.0 ± 1.4 |
| I3145 | 3.0 ± 0.0 | n.i | 13.5 ± 0.7 |
| I3149 | 2.0 ± 0.0 | n.i | n.i |
| I3153 | 2.5 ± 0.7 | 1.0 ± 0.0 | 14.0 ± 0.0 |
| L. brevis CD2 | 3.0 ± 0.0 | 2.5 ± 0.7 | 12.0 ± 0.0 |
| L. reuteri DSM17938 | n.i | 1.0 ± 0.0 | 9.0 ± 0.0 |
| S. salivarius K12 | n.i | 6.0 ± 2.8 | 10.0 ± 1.4 |

Example 9: Antagonism Against *Aggregatibacter actinomycetemcomitans*

The activity of probiotic candidates to antagonize *Aggregatibacter actinomycetemcomitans* was studied in liquid medium. Probiotic candidates and *Lactobacillus* sp. controls were grown overnight at 37° C. in microaerophilic conditions (5% $CO_2$) in MRS liquid medium. *Staphylococcus salivarius* K12 was grown in same conditions but using BHI medium. Cultures were centrifuged and supernatant filtered through 0.22 micrometers. Twenty microliters of the filtered supernatants were added to 96-well microplates containing 160 ml of BHI medium. Finally, 20 ml of a suspension of *A. actinomycetemcomitans* in PBS standardized to 1E+05 CFU/mL were added to the wells and incubated for 24 h in microaerophilic conditions (5% $CO_2$) at 37° C. *A. actinomycetemcomitans* was monitored by determining the absorbance at 625 nm. The inhibitory capacity of probiotic supernatants was determined by comparing the growth of *A.*

*actinomycetemcomitans* supplemented with probiotic supernatant and its growth without being supplemented (negative control) by using the following formula:

$$\text{Inhibition (\%)} = \frac{(DO_C - DO_B) - (DO_C - DO_P)}{(DO_C - DO_B)} \times 100$$

wherein,
$DO_C$ corresponded to the negative control and was the optical density at 625 nm of wells containing 160 μl of BHI medium+20 μl of *A. actinomycetemcomitans* suspension+20 μl of MRS or BHI,
$DO_B$ corresponded to the blank and was the optical density at 625 nm of wells containing 160 μl of BHI medium+40 μl of MRS or BHI, and
$DO_P$ corresponded to probiotic candidates and was the optical density at 625 nm of wells containing 160 μl of BHI medium+20 μl of *A. actinomycetemcomitans* suspension+20 μl of probiotic supernatant.

Figure 5:
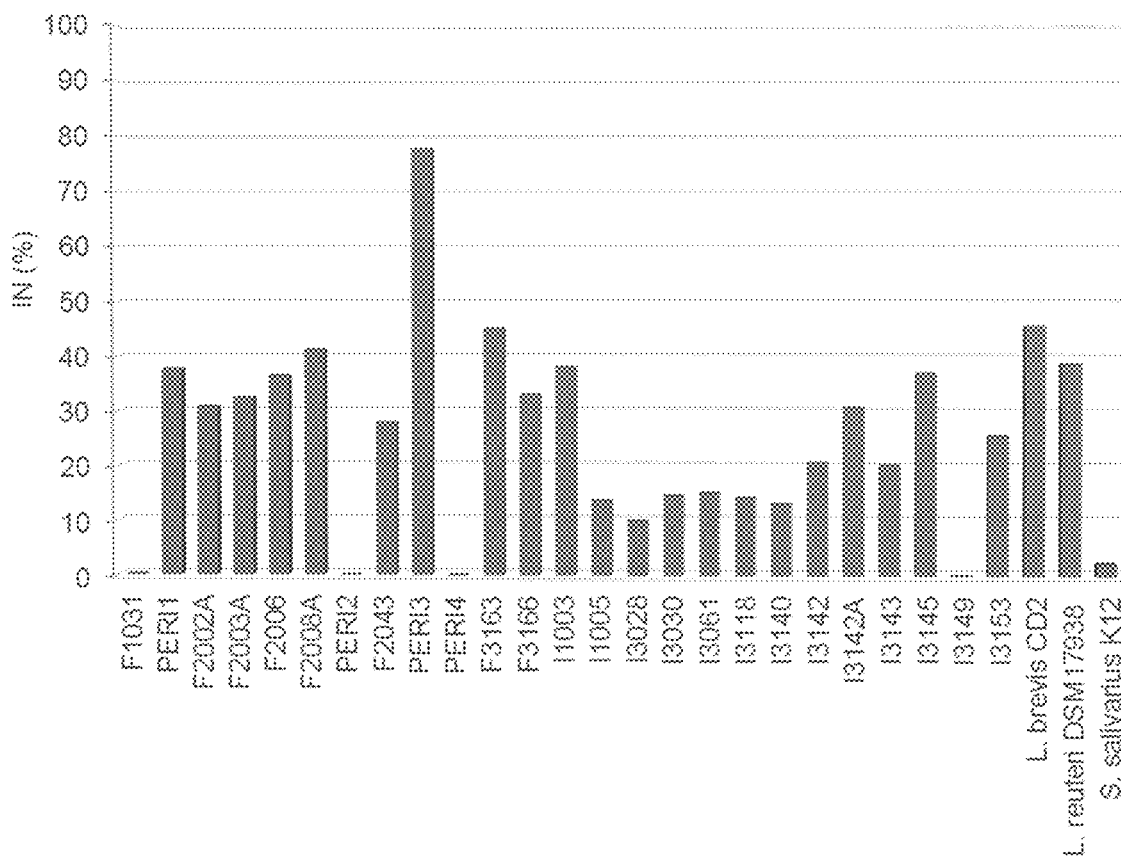
FIG. 5: Inhibitory activity (In) of probiotic candidates against *Aggregatibacter actinomycetemcomitans*.

All experiments were performed in duplicate.
Results
The inhibitory activity of the probiotic candidates against *A. actinomycetemcomitans* is depicted in FIG. 5. Among the different strains, PERI3 showed the greatest activity, being able to reduce by 77.9% the growth of *A. actinomycetemcomitans*. This activity was significantly higher than commercial controls such as *L. brevis* CD2, *L. reuteri* DSM17938 and especially *S. salivarius* K12 (45.6, 38.8 and 2.42%, respectively).

Example 10: Capacity to Form Aggregates

The capacity of bacteria to auto-aggregate is considered the first step necessary for forming a biofilm and can be used as a characteristic for assessing the potential biofilm-forming capacity of the strains. Biofilm formation allows to create a protective barrier that can reduce the attachment of pathogen to the oral surfaces. The capacity to form aggregates was evaluated for probiotic candidates PERI, PERI2, PERI3, PERI4, I3142A, I1005, I3030 and I3145. *L. brevis* CD2 and *S. salivarius* K12 were used as controls. Strains were grown overnight in MRS medium (or BHI for *S. salivarius* K12) at 37° C. and microaerophilic conditions (5% $CO_2$). After this period, cultures were centrifuged at 1000 g for 5 minutes, supernatant discarded and pellet washed twice with PBS. Finally, PBS was added until obtaining a probiotic suspension having an optical density equivalent to a McFarland standard 1 (approximately. 3E+08 CFU/mL). Three mL of the suspension were transferred to spectrophotometer cuvettes and optical density monitored at 620 nm for 3 and 6 hours. The auto-aggregation capacity at this time intervals were determined by using the following formula:

$$\text{Aggregation (\%)} = \frac{DO_0 - DO_t}{DO_0} \times 100$$

wherein $DO_0$ is the net absorbance at 620 nm of the bacterial suspension at the beginning of the test (time 0), and $DO_t$ is the net absorbance at 620 nm of the bacterial suspension at either 3 or 6 hours.
Results
Percentage of aggregation at 3 and 6 h is summarized in TABLE 3. The probiotic candidate PERI4 was the strain showing the highest auto-aggregation capacity whereas the candidate I3030 and *S. salivarius* K12 showed the lowest activity.

TABLE 3

| Percentage of aggregation of probiotic candidates | | |
|---|---|---|
| Strain | 3 h | 6 h |
| I1005 | 11.2 | 13.3 |
| I3030 | 6.9 | 6.9 |
| I3142A | 5.7 | 24.5 |
| I3145 | 5.2 | 21.1 |
| PERI1 | 8.3 | 17.2 |
| PERI2 | 6.7 | 19.7 |
| PERI3 | 4.3 | 14.7 |
| PERI4 | 3.9 | 27.8 |
| *L. brevis* CD2 | 11.1 | 26.9 |
| *S. salivarius* K12 | 0.0 | 7.9 |

Example 11: Preparation of a Reconstitutable Probiotic Gel in Powder Form for Implant Application 500 g of a freeze-dried powder containing *Pediococcus* CECT 8904, *Pediococcus* CECT 8905 and *Pediococcus* CECT 8906 at 4E+10 cfu/g, 200 g of guar gum and 300 g of hydroxyethylcellulose were mixed and homogenized. 0.5 g of this powder blend were introduced into a glass vial provided with a screw cap. Upon the addition of 2.5 ml of water, preferably deionized or distilled water, and manual shaking, the reconstituted gel was formed. The final dose of probiotic was 1E+10 cfus/vial. After reconstitution of gel, the concentration of guar gum in gel was 4% and hydroxyethylcellulose 6%.

Example 12: Preparation of a Reconstitutable Probiotic Gel in Powder Form for Implant Application 535 g of a freeze-dried powder containing *Pediococcus* CECT 8904 and *Pediococcus* CECT 8905 at 3.75E+10 cfu/g, 150 g of sodium alginate, 15 g of calcium acetate and 300 g of hydroxyethylcellulose were mixed and homogenized. 0.5 g of this powder blend were introduced into a glass vial provided with a septum and aluminum capsule. Upon the addition of 2.5 mL of water with a syringe, preferably deionized or distilled water, and manual shaking, the reconstituted gel was formed. The final dose of probiotic was 1E+10 CFU/vial. After reconstitution of gel, the concentration of alginate in gel was 3% and hydroxyethylcellulose 6%.

Example 13: Preparation of a Reconstitutable Probiotic Gel in Powder Form for Implant Application 700 g of a freeze-dried powder containing *Pediococcus* CECT 8904, *Pediococcus* CECT 8905 and *Pediococcus* CECT 8906 at 2.9E+10 cfu/g, 200 g of guar gum and 100 g of polyvinylpyrrolidone were mixed and homogenized. 0.5 g of this powder blend were introduced into a glass vial provided with a septum and aluminum capsule. Upon the addition of 2.5 mL of water with a syringe, preferably deionized or distilled water, and manual shaking, the reconstituted gel was formed. The final dose of probiotic was 1E+10 cfu/vial. After reconstitution of gel, the concentration of guar gum in gel was 4% and polyvinylpyrrolidone 2%.

Example 14: Preparation of a Reconstitutable Probiotic Gel in Powder Form for Implant Application 500 g of a freeze-dried powder containing *Pediococcus* CECT 8904, *Pediococcus* CECT 8905 and *Pediococcus* CECT 8906 at 4E+10 cfu/g, and 500 g of guar gum were mixed and homogenized. 0.5 g of this powder blend were introduced into a glass vial provided with a screw cap. Upon the addition of 6 ml of water, preferably deionized or distilled water, and manual shaking, the reconstituted gel was formed. The final dose of probiotic was 1E+10 cfus/vial. After reconstitution of gel, the concentration of guar gum in gel was 4%.

Example 15: Preparation of a Reconstitutable Probiotic Gel in Powder Form for Teeth Application 600 g of a freeze-dried powder containing *Pediococcus* CECT 8903 at 3.35E+10 cfu/g, 100 g of guar gum and 300 g of hydroxyethylcellulose were mixed and homogenized. 0.5 g of this powder blend were introduced into a glass vial provided with a screw cap. Upon the addition of 2.5 ml of water, preferably deionized or distilled water, and manual shaking, the reconstituted gel was formed. The final dose of probiotic was 1E+10 cfu/vial. After reconstitution of gel, the concentration of guar gum in gel was 2% and hydroxyethylcellulose 6%.

Example 16: Preparation of a Reconstitutable Probiotic Gel in Powder Form for Teeth Application 590 g of a freeze-dried powder containing *Pediococcus* CECT 8903 at 3.4E+10 cfu/g, 100 g of sodium alginate, 10 g of calcium acetate, and 300 g of hydroxyethylcellulose were mixed and homogenized. 0.5 g of this powder blend were introduced into a glass vial provided with a screw cap. Upon the addition of 2.5 mL of water, preferably deionized or distilled water, and manual shaking, the reconstituted gel was formed. The final dose of probiotic was 1E+10 cfu/vial. After reconstitution of gel, the concentration of alginate in gel was 2% and hydroxyethylcellulose 6%.

Example 17: Preparation of a Reconstitutable Probiotic Gel in Powder Form for Teeth Application 280 g of a freeze-dried powder containing *Pediococcus* CECT 8906 at 7E+10 cfu/g, and 720 g of hydroxyethylcellulose were mixed and homogenized. 0.5 g of this powder blend were introduced into a glass vial provided with a screw cap. Upon the addition of 6 ml of water, preferably deionized or distilled water, and manual shaking, the reconstituted gel was formed. The final dose of probiotic was 1E+10 cfus/vial. After reconstitution of gel, the concentration of hydroxyethylcellulose in gel was 6%.

Example 18: Preparation of a Reconstitutable Probiotic Gel in Powder Form for Teeth Application 600 g of a freeze-dried powder containing *Lactobacillus brevis* CD2 at 4E+10 cfu/g, 100 g of guar gum and 300 g of hydroxyethylcellulose were mixed and homogenized. 0.5 g of this powder blend were introduced into a glass vial provided with a screw cap. Upon the addition of 2.5 ml of water, preferably deionized or distilled water, and manual shaking, the reconstituted gel was formed. The final dose of probiotic was 1E+10 cfu/vial. After reconstitution of gel, the concentration of guar gum in gel was 2% and hydroxyethylcellulose 6%.

Example 19: Preparation of a Reconstitutable Probiotic Gel in Powder Form for Teeth Application 590 g of a freeze-dried powder containing *Lactobacillus brevis* CD2 at 4E+10 cfu/g, 100 g of sodium alginate, 10 g of calcium acetate, and 300 g of hydroxyethylcellulose were mixed and homogenized. 0.5 g of this powder blend were introduced into a glass vial provided with a screw cap. Upon the addition of 2.5 mL of water, preferably deionized or distilled water, and manual shaking, the reconstituted gel was formed. The final dose of probiotic was 1E+10 cfu/vial. After reconstitution of gel, the concentration of alginate in gel was 2% and hydroxyethylcellulose 6%.

Example 20: Preparation of a Reconstitutable Probiotic Gel in Powder Form for Teeth Application 700 g of a freeze-dried powder containing *Streptococcus salivarius* K12 at 2.9E+10 cfu/g, 200 g of guar gum and 100 g of polyvinylpyrrolidone were mixed and homogenized. 0.5 g of this powder blend were introduced into a glass vial provided with a septum and aluminum capsule. Upon the addition of 2.5 mL of water with a syringe, preferably deionized or distilled water, and manual shaking, the reconstituted gel was formed. The final dose of probiotic was 1E+10 cfu/vial. After reconstitution of gel, the concentration of guar gum in gel was 4% and polyvinylpyrrolidone 2%.

Example 21. Application of the Reconstitutable Probiotic Gel in a Patient with Peri-Implantitis The crown was removed and local anesthesia was administered to the patient. The zone was cleaned and the subgingival plaque mechanically removed. Chlorhexidine 0.12% was administered and after that, saline solution. The reconstituted gel of Example 11 was obtained by adding 2.5 mL of sterile water to the freeze-dried powder containing *Pediococcus* CECT 8904, *Pediococcus* CECT 8905 and *Pediococcus* CECT 8906 at 4E+10 cfu/g, 200 g of guar gum and 300 g of hydroxyethylcellulose and vigorously mixing for 1 minute. The mixture was allowed to stand at room temperature for a period between 1 and 10 minutes and administered to the peri-implant pocket with a syringe and needle with blunt tip, positioning the tip of the blunt needle close to the base of the pocket and injecting the product until the solution reaches the upper edge of the gum. Then, after drawing the needle out of the pocket, saline solution washings and an air jet (during ca. 10 sec.) were applied on the treated zone. Immediately after, the crown was put in place. The patient was instructed not to brush the teeth within 6 hours post-treatment.

Example 22. Application of the Reconstitutable Probiotic Gel in a Patient for the Prevention of Caries Teeth were cleaned with a toothbrush and cleared of heavy plaque or debris. The teeth to be treated were lightly dried with air and isolated with cotton rolls to prevent recontamination with saliva. A small amount of gel (0.5 ml) made following Example 15 was dispensed by means of a brush to the teeth. The patient was instructed to avoid brushing for the rest of the day.

Example 23. Application of the Reconstitutable Probiotic Gel in a Patient for the Prevention of Caries Teeth were cleaned with a toothbrush and cleared of heavy plaque or debris. A self-film-forming composition comprising 50 mg of probiotic strain, 120 mg of guar gum and 360 mg of hydroxyethylcellulose was reconstituted with 6 mL of water and immediately aspired with a syringe. The gel was allowed to stand for 1 minute in the syringe and then uniformly distributed in a mouth splint. Subsequently, the splint was immediately applied in the mouth and removed after 5 minutes. The patient was provided with more vials containing the self-film-forming composition and instructed to follow the same procedure for self-administrating the reconstituted gel each 48 hours, preferably at night after brushing their teeth, just before going to sleep. Patients were instructed not to bush their teeth, eat or drink after applying the gel.

Example 24: Efficacy Study of the Reconstitutable Probiotic Gel in Animal Model

The efficacy of the probiotic gel on the prevention of mucositis and peri-implantitis was studied in Beagle dog as animal model. All procedures were conducted under the supervision of a veterinary surgeon. Animals were pre-anesthetized with acepromazine (0.12%-0.25 mg/kg), buprenorphine (0.01 mg/kg) and medetomidine (35 lg/kg) by intramuscular injection in the femoral quadriceps. An intravenous catheter was inserted (diameter 22 or 20 gauge) into the cephalic vein, and propofol infused at the rate of 0.4 mg/kg/min at a slow constant infusion rate. Conventional dental infiltration anaesthesia (articaine 40 mg, 1% epinephrine) was administered at the surgical sites. Both quadrants of the lower jaws, second premolars (PM2) and first molars (M1) were used as experimental sites. Teeth were sectioned with a carbide tungsten drill and roots removed with forceps, without damaging the remaining bony walls. Sulcular marginal incisions were made along the vestibular and lingual areas adjoining the alveoli, separating tissues to make crestal hard tissue walls visible. After two months of site healing 8 implants were crestally placed and allowed to heal for another two more months with healing cups. After the two months of healing, silk ligatures were placed around each abutment. Oral gels were also administered around the implants. Five dogs were treated with a reconstituted liquid gel containing 4% of guar gum, 6% hydroxyethylcellulose and 4 CFU per mL of a probiotic mixture composed by *Pediococcus* CECT 8904, *Pediococcus* CECT 8905 and *Pediococcus* CECT 8906 (1:1:1). One of the animals was treated with the same gel, but not containing probiotic. The animals were then fed a soft diet to induce plaque accumulation and to provoke peri-implant inflammation and loss of bone. Additional ligatures were placed over the previous ones and around the implants every two weeks.

Healing was uneventful after all surgeries, no exposure or secondary wound healing was observed. The experimental peri-implantitis resulted in signs of inflammation and bone loss. Generally, animals treated with probiotic gel showed less pronounced tissue loss, inflammatory response, probing depth, mucosal recession, and bleeding on probing, compared to the animal treated with gel not containing probiotic. Therefore, probiotic treatment ameliorated clinical signs associated with peri-implantitis.

Example 25: Study of Rheological Properties of Gelifier and Bioadhesive Agents

The viscosity and adhesiveness of different agents was studied. The following compositions were studied:
Sodium alginate at concentrations ranging from 2 to 8% in water (w/v), with or without calcium acetate at concentrations (0.02-0.2%).
Guar gum at concentrations ranging from 1 to 5% in water (w/v).
Methylcellulose at concentrations ranging from 1 to 5% in water (w/v).
Hydroxyethylcellulose at concentrations ranging from 1 to 6% in water (w/v).
Sodium carboxymethylcellulose at concentrations ranging from 1 to 3% in water (w/v).

TABLE 4

Viscosity and adhesiveness capacity:

| Agent | Viscosity | Adhesiveness | Observations |
|---|---|---|---|
| Sodium alginate | High | Very low | Lump formation at high concentrations |
| Guar gum | Very high | Very low | Good solubility |
| Methylcellulose | Low | Very low | Foam formation under agitation |
| Hydroxyethylcellulose | Very low | Very high | Good solubility |
| Carboxymethylcellulose | Very low | Low | Good solubility |

The viscosity and adhesiveness conferred to the film-forming compositions was dependent on the agent used offering different possibilities depending on the clinical application of the gel. Combinations with sodium alginate and, especially, guar gum with hydroxyethylcellulose were considered good candidates to form gels combining properties such as high viscosity and adhesiveness.

BIBLIOGRAPHIC REFERENCES

Patent Literature

JP20100053062—Sunstar Inc. 11 Mar. 2010.

Non-Patent Literature

Albertini, M. et al. "Assessment of periodontal and opportunistic flora in patients with peri-implantitis". Clinical Oral Implants Research 2014, vol. 00 p. 1-4
Da Silva, E. S. C. et al. "Microbial diversity of peri-implantitis biofilm by Sanger Sequencing". Clin Oral Implants Research 2013, vol. 0, p. 1-8
Persson, G. R. et al. "Cluster of Bacteria Associated with Peri-Implantitis". Clinical Implant Dentistry and related research 2013, vol. 0, p. 1-11
Ata-Ali, J. et al. "Peri-implantitis: Associated microbiota and treatment". Med Oral Patol Oral Cir Bucal. 2011, vol. 16, p. 937-43
Flötra, L. et al. "Side effects of chlorhexidine mouth washes". Scand J Dent Res 1971, vol. 73, p. 119-125
Slots, J. et al. "Antibiotics in periodontal therapy: advantages and disadvantages". J Clin Periodontol 1990, vol. 17, p. 479-493

Szkaradkiewicz, A. K. et al. "Effect of Oral Administration Involving a Probiotic Strain of *Lactobacillus reuteri* on Pro-Inflammatory Cytokine Response in Patients with Chronic Periodontitis". Arch Immunol Ther Exp (Warsz) 2014, vol. 62, p. 495-500

Teughels, W. et al. "Clinical and microbiological effects of *Lactobacillus reuteri* probiotics in the treatment of chronic periodontitis: a randomized placebo-controlled study" J of clinical periodontology 2013, vol. 40 p. 1025-35

Hallstroem, H. et al. "Effect of probiotic lozenges on inflammatory reactions and oral biofilm during experimental gingivitis". Acta Odontologica Scandinavica 2013, vol. 71, p. 828-833

Flichy-Fernandez, A. J. et al. "The effect of orally administered probiotic *Lactobacillus reuteri*-containing tablets in peri-implant mucositis: a double-blind randomized controlled trial". J Periodont Res 2015, Epub ahead of print Toiviainen, A. et al., "Impact of orally administered lozenges with *Lactobacillus rhamnosus* GG and *Bifidobacterium animalis* subsp. *lactis* BB-12 on the number of salivary mutans streptococci, amount of plaque, gingival inflammation and the oral microbiome in healthy adults". Clin Oral Investig 2015, vol. 19, p. 77-83

Maekawa, T. et al. "Topical treatment with probiotic *Lactobacillus brevis* CD2" inhibits experimental periodontal inflammation and bone loss" J Periodont Res 214, vol. 44, p. 785-791

Yanine, N. et al. "Effects of probiotics in periodontal diseases: a systematic review". Clinical oral investigations 2013, vol. 17, p. 1627-34

Andreoletti, O. et al. "The maintenance of the list of QPS microorganisms intentionally added to food or feed. Question no: EFSA-Q-2008-006". The EFSA Journal 2008, vol. 923, p. 1-48

Weisburg, W. G. et al. "16S ribosomal DNA amplification for phylogenetic study". J Bacteriology 1991, vol. 173, p. 697-703

Muyzer, G. et al. "Application of denaturing gradient gel electrophoresis (DGGE) and temperature gradient gel electrophoresis (TGGE) in microbial ecology". Antonie van Leeuwenhoeck 1998, vol. 73, p. 127-141

Nigatu, A. et al. "Randomly amplified polymorphic DNA (RAPD) for discrimination of *Pediococcus pentosaceus* and *Pediococcus acidilactici* and rapid grouping of *Pediococcus* isolates" Letters in Applied Microbiology 1998, vol. 26, p. 412-6

The invention claimed is:

1. An oral composition comprising:
   (i) at least one gelifier agent in powder form,
   (ii) at least one bioadhesive agent in powder form, and
   (iii) at least one lactic acid bacteria strain belonging to genus *Pediococcus* in powder form,
   wherein the (i) at least one gelifier agent is in an amount of 0.05-90% w/w of the composition in powder form to provide viscosity to the composition, and is selected from the group consisting of: (a) a starch, (b) a gum, (c) an algal polysaccharide, (d) a polysaccharide selected from the group consisting of pectin and maltodextrin, (e) a cellulose derivative, (f) a polypeptide selected from the group consisting of gelatin, collagen, and casein;
   wherein the (ii) at least one bioadhesive agent is in an amount of 0.05%-90% w/w of the composition in powder form to provide adhesiveness to the composition, and is selected from the group consisting of: (a) a gum, (b) an algal polysaccharide, (c) a cellulose derivative, (d) a polysaccharide selected from the group consisting of pectin and maltodextrin, and (e) a polymer selected from the group consisting of an acrylate-based polymer, a vinyl-based polymer and a cationic polysaccharide; and
   wherein the composition is a powder and subsequently forms a film under agitation in the presence of a liquid medium upon topical administration to an oral cavity.

2. The oral composition of claim 1, wherein the gelifier agent and the bioadhesive agent have no bactericidal effect against the at least one lactic acid bacteria.

3. The oral composition of claim 2, wherein the gelifier agent and the bioadhesive agent have no bacteriostatic effect against the at least one lactic acid bacteria.

4. The oral composition of claim 3, wherein the gelifier agent or the bioadhesive agent have prebiotic effect on the at least one lactic acid bacteria.

5. The oral composition of claim 1, wherein the gelifier agent is selected from the group consisting of a gum and an algal polysaccharide and the bioadhesive agent is selected from the group consisting of a cellulose derivative and a vinyl-based polymer.

6. The oral composition of claim 1, wherein the *Pediococcus* strain is selected from the group consisting of: strain deposited under accession number CECT 8903, strain CECT 8904, strain CECT 8905, and strain CECT 8906.

7. The oral composition of claim 1,
   wherein the oral composition and the liquid medium are in a single or in separate containers.

8. The oral composition according to claim 7, wherein the bacteria strain is selected from the group consisting of: strain deposited under accession number CECT 8903, strain CECT 8904, strain CECT 8905, strain CECT 8906.

9. The oral composition of claim 1, wherein the at least one gelifier agent is not a cellulose derivative and the at least one bioadhesive agent is selected from a cellulose derivative and a vinyl-based polymer.

10. The oral composition of claim 1, wherein the amount of gelifier agent and bioadhesive agent in the composition is from 0.05 to 20% (w/v) for each agent.

11. A process for preparing a reconstituted formula comprising mixing under agitation the oral composition of claim 1 with a liquid medium.

12. A reconstituted formula obtained by the process of claim 11.

13. The reconstituted formula according to claim 12, wherein the amount of gelifier agent and bioadhesive agent in the reconstituted formula is from 0.05 to 20% (w/v) for each agent.

14. The reconstituted formula according to claim 13, wherein the amount of gelifier agent is from 1 to 5% (w/v) and the amount of bioadhesive agent is from 4 to 10% (w/v).

15. A method of using the oral composition of in claim 1, comprising a step of administering the oral composition to a subject.

16. A method of treating a subject having a condition selected from the group consisting of: peri-implantitis, mucositis, periodontitis, gum disease, caries, oral candidiasis, cold sores and blisters, said method comprises administering the oral composition of claim 1 to the subject.

17. The method of claim 16 wherein the bacteria strain is selected from the group consisting of: strain deposited under accession number CECT 8903, strain CECT 8904, strain CECT 8905, and strain CECT 8906.

18. A kit for oral use, comprising:
1) the oral composition of claim 1; and
2) means to apply to the buccal cavity the oral composition.

* * * * *